(12) United States Patent
Haberland et al.

(10) Patent No.: US 12,606,828 B2
(45) Date of Patent: Apr. 21, 2026

(54) **APTAMERS FOR USE IN THE TREATMENT OF *CORONAVIRIDAE* INFECTIONS**

(71) Applicant: Berlin Cures GmbH, Berlin (DE)

(72) Inventors: Annekathrin Haberland, Berlin (DE); Johannes Müller, Berlin (DE); Gerd Wallukat, Berlin (DE); Peter Göttel, Falkensee (DE)

(73) Assignee: APTA Therapeutics GmbH, Berlin (DE)

( * ) Notice: Subject to any disclaimer, the term of this patent is extended or adjusted under 35 U.S.C. 154(b) by 739 days.

(21) Appl. No.: 17/995,705

(22) PCT Filed: Apr. 9, 2021

(86) PCT No.: PCT/EP2021/059328
§ 371 (c)(1),
(2) Date: Oct. 6, 2022

(87) PCT Pub. No.: WO2021/205012
PCT Pub. Date: Oct. 14, 2021

(65) Prior Publication Data
US 2023/0140490 A1 May 4, 2023

(30) Foreign Application Priority Data

| | | |
|---|---|---|
| Apr. 9, 2020 | (EP) | 20168929 |
| May 22, 2020 | (EP) | 20176023 |
| Jun. 18, 2020 | (EP) | 20180781 |
| Oct. 27, 2020 | (EP) | 20204036 |

(51) Int. Cl.
| | |
|---|---|
| *C12N 15/115* | (2010.01) |
| *A61P 31/14* | (2006.01) |
| *C12N 15/113* | (2010.01) |

(52) U.S. Cl.
CPC .......... *C12N 15/1131* (2013.01); *A61P 31/14* (2018.01); *C12N 2310/16* (2013.01)

(58) Field of Classification Search
CPC ............ C12N 15/1131; C12N 2310/16; C12N 15/115; C12N 2320/30; A61P 31/14; A61K 31/7088
See application file for complete search history.

(56) References Cited

U.S. PATENT DOCUMENTS 7,998,939 B2 * 8/2011 Diener ...................... A61P 7/08
536/23.1

OTHER PUBLICATIONS

JP Office Action for corresponding JP Application No. 2022-561426, dated Apr. 8, 2025, 5.
"SARS-CoV-2 Spike RBD LlaMABody VHH Domain Antibody"; Funakoshi Frontiers in Life Science; R& D Systems, Inc.; https://www.funakoshi.com.jp/contents/69353; May 16, 2022; 8 pages.
PCT International Search Report and Written Opinion for PCT/EP2021/059328, mailed Jun. 30, 2021 (14 pages).
Cho, et al., "Novel System for Detecting SARS Coronavirus Nucleocapsid Protein Using an ssDNA Aptamer", Journal of Bioscience and Bioengineering, 112(6), pp. 535-540, 2011.
Jin, et al., "Isolation of Inhibitory RNA Aptamers Against Severe Acute Respiratory Syndrome (SARS) Coronavirus NTPase/Helicase," Biochemical and Biophysical Research Communications, 366, pp. 738-744, 2008.
Roxo, et al., "G-Quadruplex-Forming Aptamers—Characteristics, Applications, and Perspectives," Molecules, 24, 3781, 2019.
Shum et al., "Differential Inhibitory Activities and Stabilisation of DNA Aptamers Against the SARS Coronavirus Helicase," ChemBioChem, 9, pp. 3037-3045, 2008.
Song, et al., "Discovery of Aptamers Targeting Receptor-Binding Domain of the SARS-CoV-2 Spike Glycoprotein," Analytical Chemistry, 92, pp. 9895-9900, 2020.
Tan, et al., "The SARS-Unique Domain (SUD) of SARS Coronovirus Contains Two Macrodomains That Bind G-Quadruplexes," PLoS Pathogens, 5(5), e1000428, 2009.
Tucker, et al., "G-Quadruplex DNA Aptamers and Their Ligands: Structure, Function, and Application," Current Pharmaceutical Design, 18, pp. 2014-2026, 2012.

* cited by examiner

*Primary Examiner* — J. E. Angell
(74) *Attorney, Agent, or Firm* — Eversheds-Sutherland (US) LLP

(57) ABSTRACT

The present invention relates to new aptamer molecules for use in therapy of infections caused by viruses from the Coronaviridae family, a method of preventing infection caused by viruses from the Coronaviridae family in vitro/ex vivo, a pharmaceutical composition and a kit comprising such aptamer molecules, and the use of aptamer molecules for preventing infection of somatic cells with a virus from the Coronaviridae family. The present invention also relates to affinity molecules binding to specific and newly identified epitopes of a key enzyme of Coronaviridae viruses.

7 Claims, 12 Drawing Sheets

Specification includes a Sequence Listing.

FIG. 4

A
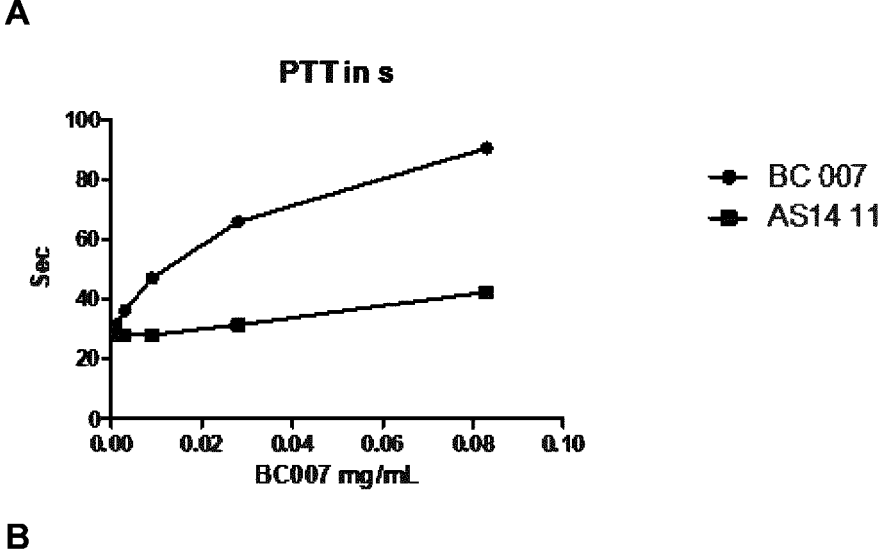
B
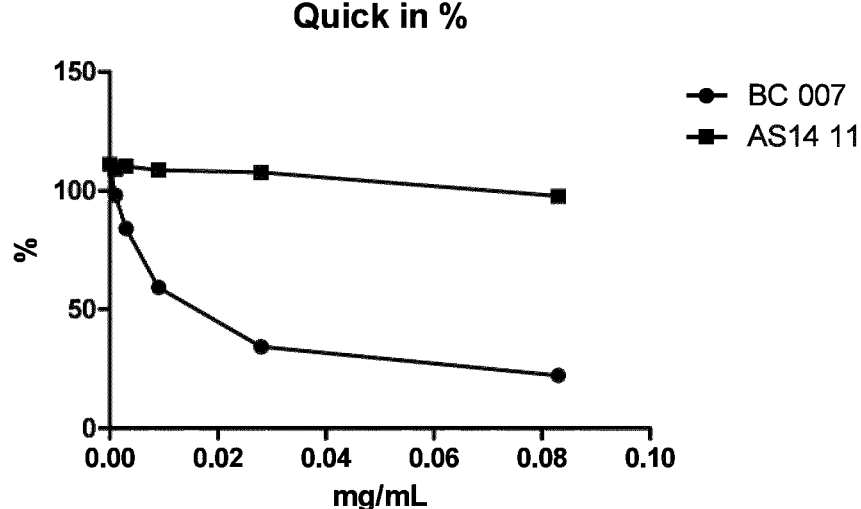
Figure 5

| Patient no. | Gender | Age (years) | Running no. | Symptom Class Neuro* | Symptom Class Cardiovasc** | Symptoms Neuro* |
|---|---|---|---|---|---|---|
| 1 | f | 48 | 1 | X | X | Fatigue, Alopecia, Anomic Aphasia |
| 7 | f | 55 | 2 | X | X | Fatigue, Alopecia |
| 11 | f | 39 | 3 | X | X | Fatigue, Alopecia |
| 19 | f | 34 | 4 | X | X | Fatigue, PoTS, Tremor |
| 22 | f | 34 | 5 | X | X | Fatigue, Alopecia |
| 3 | f | 56 | 6 | X | X | Fatigue, Attention Deficit |
| 21 | f | 28 | 7 | X | X | Attention Deficit, Tremor, Dysautonomia |
| 18 | f | 53 | 8 | X | X | Tremor, Attention Deficit |
| 20 | m | 54 | 9 | X | X | Attention Deficit |
| 14 | f | 57 | 10 | X | X | Fatigue, Anomic Aphasia |
| 23 | f | 50 | 11 | X | X | Eczema, Alopecia |
| 24 | f | 33 | 12 | X | X | Fatigue, PoTS |
| 2 | m | 42 | 13 | X | — | Fatigue, Alopecia |
| 4 | m | 50 | 14 | X | — | Fatigue |
| 5 | f | 45 | 15 | X | — | Fatigue |
| 6 | f | 36 | 16 | X | — | Tremor, Alopecia, Dysautonomia |
| 9 | f | 50 | 17 | X | — | Fatigue |
| 10 | f | 48 | 18 | X | — | Fatigue |
| 12 | f | 53 | 19 | X | — | Fatigue, Attention Deficit |
| 15 | f | 46 | 20 | X | — | Fatigue, Alopecia, Polyneuropathy |
| 17 | f | 49 | 21 | X | — | Fatigue, PoTS, Tremor |
| 25 | f | 58 | 22 | X | — | Attention Deficit, Neuropathy |
| 13 | f | 26 | 23 | X | — | Fatigue |
| 8 | m | 71 | 24 | — | ⋯ | Symptom Free |
| 16 | m | 54 | 25 | — | — | Symptom Free |

FIG. 10

| Cardiovasc** | Neuro-active AABs | | Vasoactive AABs | | Nero-and Vasoactive AABs | RAS-Specific AABs | |
|---|---|---|---|---|---|---|---|
| | Noc-AAB+ | β2-AAB$ | α1-AAB& | ETA-AAB+ | M2-AAB% | AT1-AAB? | MAS-AAB+ |
| Tachycardia | X | X | | X | X | X | X |
| Tachycardia | X | X | X | X | X | X | X |
| Tachycardia | X | X | | | X | X | X |
| Tachycardia | | X | X | | X | X | X |
| Tachycardia | | X | X | X | X | X | X |
| Tachycardia | X | X | X | | X | X | X |
| Arrhythmia | | X | | | X | | X |
| Tachycardia | | X | | | | | |
| Tachycardia, Hypertension | X | X | | | X | X | X |
| Arrhythmia, Hypertension | | X | | | X | X | X |
| Myocarditis | X | X | X | X | X | X | X |
| n.a. | | X | | | X | X | X |
| n.a. | | X | | | X | X | X |
| n.a. | | X | | | X | X | X |
| n.a. | X | X | X | X | X | X | X |
| n.a. | X | X | | | X | X | X |
| n.a. | | X | | | X | X | X |
| n.a. | X | X | X | X | X | X | X |
| n.a. | X | X | | | X | X | X |
| n.a. | | X | | X | X | X | X |
| n.a. | | X | | | X | X | X |
| n.a. | X | X | X | X | X | X | X |
| Symptom Free | | X | | | X | X | X |
| Symptom Free | | X | | | | | X |

FIG. 10 (Continued)

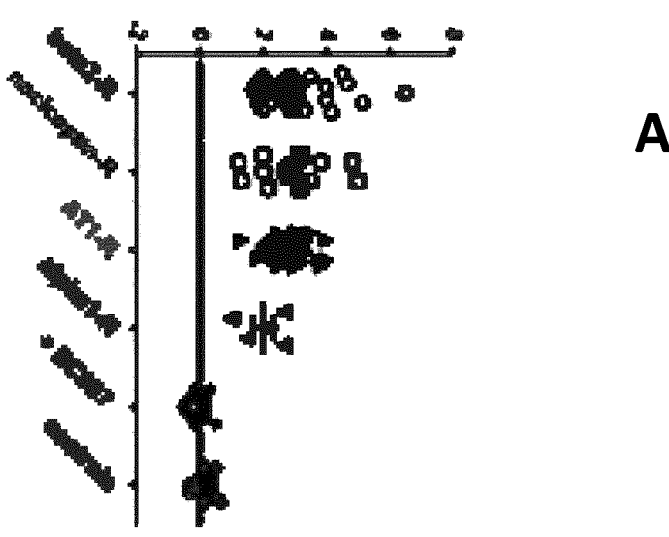
A
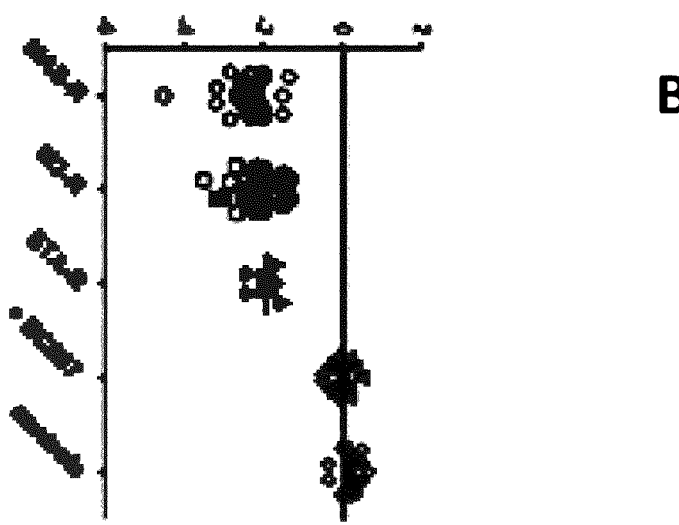
B
Figure 11

SEQUENCE LISTING

```
<160> NUMBER OF SEQ ID NOS: 11

<210> SEQ ID NO 1
<211> LENGTH: 15
<212> TYPE: DNA
<213> ORGANISM: Artificial Sequence
<220> FEATURE:
<223> OTHER INFORMATION: Aptamer BC007

<400> SEQUENCE: 1
ggttggtgtg gttgg                                                        15

<210> SEQ ID NO 2
<211> LENGTH: 223
<212> TYPE: PRT
<213> ORGANISM: Severe acute respiratory syndrome-related coronavirus 2
<220> FEATURE:
<223> OTHER INFORMATION: Receptor-binding domain (RBD) of S1 Subunit of
      Spike protein of SARS-CoV-2

<400> SEQUENCE: 2

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
            115                 120                 125

Gly Asn Tyr Asn Tyr Leu Tyr Arg Leu Phe Arg Lys Ser Asn Leu Lys
        130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175
```

-continued

```
Tyr Gly Phe Gln Pro Thr Asn Gly Val Gly Tyr Gln Pro Tyr Arg Val
              180                 185                 190

Val Val Leu Ser Phe Glu Leu Leu His Ala Pro Ala Thr Val Cys Gly
          195                 200                 205

Pro Lys Lys Ser Thr Asn Leu Val Lys Asn Lys Cys Val Asn Phe
    210                 215                 220
```

```
<210> SEQ ID NO 3
<211> LENGTH: 222
<212> TYPE: PRT
<213> ORGANISM: Severe acute respiratory syndrome-related coronavirus
<220> FEATURE:
<223> OTHER INFORMATION: Receptor-binding domain of S1 subunit of Spike
      protein of SARS-CoV

<400> SEQUENCE: 3
```

```
Arg Val Val Pro Ser Gly Asp Val Val Arg Phe Pro Asn Ile Thr Asn
1               5                   10                  15

Leu Cys Pro Phe Gly Glu Val Phe Asn Ala Thr Lys Phe Pro Ser Val
              20                  25                  30

Tyr Ala Trp Glu Arg Lys Lys Ile Ser Asn Cys Val Ala Asp Tyr Ser
          35                  40                  45

Val Leu Tyr Asn Ser Thr Phe Phe Ser Thr Phe Lys Cys Tyr Gly Val
      50                  55                  60

Ser Ala Thr Lys Leu Asn Asp Leu Cys Phe Ser Asn Val Tyr Ala Asp
65                  70                  75                  80

Ser Phe Val Val Lys Gly Asp Asp Val Arg Gln Ile Ala Pro Gly Gln
                  85                  90                  95

Thr Gly Val Ile Ala Asp Tyr Asn Tyr Lys Leu Pro Asp Asp Phe Met
              100                 105                 110

Gly Cys Val Leu Ala Trp Asn Thr Arg Asn Ile Asp Ala Thr Ser Thr
              115                 120                 125

Gly Asn Tyr Asn Tyr Lys Tyr Arg Tyr Leu Arg His Gly Lys Leu Arg
    130                 135                 140

Pro Phe Glu Arg Asp Ile Ser Asn Val Pro Phe Ser Pro Asp Gly Lys
145                 150                 155                 160

Pro Cys Thr Pro Pro Ala Leu Asn Cys Tyr Trp Pro Leu Asn Asp Tyr
              165                 170                 175

Gly Phe Tyr Thr Thr Thr Gly Ile Gly Tyr Gln Pro Tyr Arg Val Val
              180                 185                 190

Val Leu Ser Phe Glu Leu Leu Asn Ala Pro Ala Thr Val Cys Gly Pro
          195                 200                 205

Lys Leu Ser Thr Asp Leu Ile Lys Asn Gln Cys Val Asn Phe
    210                 215                 220
```

```
<210> SEQ ID NO 4
<211> LENGTH: 240
<212> TYPE: PRT
<213> ORGANISM: Middle East respiratory syndrome-related coronavirus
<220> FEATURE:
<223> OTHER INFORMATION: Receptor-binding domain of S1 subunit of Spike
      protein of MERS-CoV

<400> SEQUENCE: 4
```

```
Glu Ala Lys Pro Ser Gly Ser Val Val Glu Gln Ala Glu Gly Val Glu
1               5                   10                  15

Cys Asp Phe Ser Pro Leu Leu Ser Gly Thr Pro Pro Gln Val Tyr Asn
              20                  25                  30
```

```
Phe Lys Arg Leu Val Phe Thr Asn Cys Asn Tyr Asn Leu Thr Lys Leu
        35                  40                  45

Leu Ser Leu Phe Ser Val Asn Asp Phe Thr Cys Ser Gln Ile Ser Pro
        50                  55                  60

Ala Ala Ile Ala Ser Asn Cys Tyr Ser Ser Leu Ile Leu Asp Tyr Phe
65                  70                  75                  80

Ser Tyr Pro Leu Ser Met Lys Ser Asp Leu Ser Val Ser Ser Ala Gly
                85                  90                  95

Pro Ile Ser Gln Phe Asn Tyr Lys Gln Ser Phe Ser Asn Pro Thr Cys
                100                 105                 110

Leu Ile Leu Ala Thr Val Pro His Asn Leu Thr Thr Ile Thr Lys Pro
                115                 120                 125

Leu Lys Tyr Ser Tyr Ile Asn Lys Cys Ser Arg Leu Leu Ser Asp Asp
        130                 135                 140

Arg Thr Glu Val Pro Gln Leu Val Asn Ala Asn Gln Tyr Ser Pro Cys
145                 150                 155                 160

Val Ser Ile Val Pro Ser Thr Val Trp Glu Asp Gly Asp Tyr Tyr Arg
                165                 170                 175

Lys Gln Leu Ser Pro Leu Glu Gly Gly Gly Trp Leu Val Ala Ser Gly
                180                 185                 190

Ser Thr Val Ala Met Thr Glu Gln Leu Gln Met Gly Phe Gly Ile Thr
                195                 200                 205

Val Gln Tyr Gly Thr Asp Thr Asn Ser Val Cys Pro Lys Leu Glu Phe
        210                 215                 220

Ala Asn Asp Thr Lys Ile Ala Ser Gln Leu Gly Asn Cys Val Glu Tyr
225                 230                 235                 240

<210> SEQ ID NO 5
<211> LENGTH: 6
<212> TYPE: PRT
<213> ORGANISM: Severe acute respiratory syndrome-related coronavirus 2
<220> FEATURE:
<223> OTHER INFORMATION: Amino acids 135-140 of SEQ ID NO: 1

<400> SEQUENCE: 5

Tyr Arg Leu Phe Arg Lys
1               5

<210> SEQ ID NO 6
<211> LENGTH: 68
<212> TYPE: DNA
<213> ORGANISM: Artificial Sequence
<220> FEATURE:
<223> OTHER INFORMATION: Anti-Influenza Aptamer A22

<400> SEQUENCE: 6
aattaaccct cactaaaggg ctgagtctca aaaccgcaat acactggttg tatggtcgaa      60
taagttaa                                                              68

<210> SEQ ID NO 7
<211> LENGTH: 26
<212> TYPE: DNA
<213> ORGANISM: Artificial Sequence
<220> FEATURE:
<223> OTHER INFORMATION: Aptamer AS 1411

<400> SEQUENCE: 7
ggtggtggtg gttgtggtgg tggtgg                                          26
```

-continued

```
<210> SEQ ID NO 8
<211> LENGTH: 932
<212> TYPE: PRT
<213> ORGANISM: Severe acute respiratory syndrome-related coronavirus 2
<220> FEATURE:
<223> OTHER INFORMATION: RNA dependent RNA polymerase from SARS-CoV-2
      virus

<400> SEQUENCE: 8

Ser Ala Asp Ala Gln Ser Phe Leu Asn Arg Val Cys Gly Val Ser Ala
1               5                   10                  15

Ala Arg Leu Thr Pro Cys Gly Thr Gly Thr Ser Thr Asp Val Val Tyr
            20                  25                  30

Arg Ala Phe Asp Ile Tyr Asn Asp Lys Val Ala Gly Phe Ala Lys Phe
            35                  40                  45

Leu Lys Thr Asn Cys Cys Arg Phe Gln Glu Lys Asp Glu Asp Asp Asn
        50                  55                  60

Leu Ile Asp Ser Tyr Phe Val Val Lys Arg His Thr Phe Ser Asn Tyr
65                  70                  75                  80

Gln His Glu Glu Thr Ile Tyr Asn Leu Leu Lys Asp Cys Pro Ala Val
                85                  90                  95

Ala Lys His Asp Phe Phe Lys Phe Arg Ile Asp Gly Asp Met Val Pro
            100                 105                 110

His Ile Ser Arg Gln Arg Leu Thr Lys Tyr Thr Met Ala Asp Leu Val
            115                 120                 125

Tyr Ala Leu Arg His Phe Asp Glu Gly Asn Cys Asp Thr Leu Lys Glu
        130                 135                 140

Ile Leu Val Thr Tyr Asn Cys Cys Asp Asp Asp Tyr Phe Asn Lys Lys
145                 150                 155                 160

Asp Trp Tyr Asp Phe Val Glu Asn Pro Asp Ile Leu Arg Val Tyr Ala
            165                 170                 175

Asn Leu Gly Glu Arg Val Arg Gln Ala Leu Leu Lys Thr Val Gln Phe
            180                 185                 190

Cys Asp Ala Met Arg Asn Ala Gly Ile Val Gly Val Leu Thr Leu Asp
            195                 200                 205

Asn Gln Asp Leu Asn Gly Asn Trp Tyr Asp Phe Gly Asp Phe Ile Gln
        210                 215                 220

Thr Thr Pro Gly Ser Gly Val Pro Val Val Asp Ser Tyr Tyr Ser Leu
225                 230                 235                 240

Leu Met Pro Ile Leu Thr Leu Thr Arg Ala Leu Thr Ala Glu Ser His
            245                 250                 255

Val Asp Thr Asp Leu Thr Lys Pro Tyr Ile Lys Trp Asp Leu Leu Lys
            260                 265                 270

Tyr Asp Phe Thr Glu Glu Arg Leu Lys Leu Phe Asp Arg Tyr Phe Lys
            275                 280                 285

Tyr Trp Asp Gln Thr Tyr His Pro Asn Cys Val Asn Cys Leu Asp Asp
        290                 295                 300

Arg Cys Ile Leu His Cys Ala Asn Phe Asn Val Leu Phe Ser Thr Val
305                 310                 315                 320

Phe Pro Pro Thr Ser Phe Gly Pro Leu Val Arg Lys Ile Phe Val Asp
            325                 330                 335

Gly Val Pro Phe Val Val Ser Thr Gly Tyr His Phe Arg Glu Leu Gly
            340                 345                 350

Val Val His Asn Gln Asp Val Asn Leu His Ser Ser Arg Leu Ser Phe
            355                 360                 365
```

-continued

```
Lys Glu Leu Leu Val Tyr Ala Ala Asp Pro Ala Met His Ala Ala Ser
    370             375             380

Gly Asn Leu Leu Leu Asp Lys Arg Thr Thr Cys Phe Ser Val Ala Ala
385             390             395             400

Leu Thr Asn Asn Val Ala Phe Gln Thr Val Lys Pro Gly Asn Phe Asn
                405             410             415

Lys Asp Phe Tyr Asp Phe Ala Val Ser Lys Gly Phe Phe Lys Glu Gly
            420             425             430

Ser Ser Val Glu Leu Lys His Phe Phe Phe Ala Gln Asp Gly Asn Ala
        435             440             445

Ala Ile Ser Asp Tyr Asp Tyr Tyr Arg Tyr Asn Leu Pro Thr Met Cys
    450             455             460

Asp Ile Arg Gln Leu Leu Phe Val Val Glu Val Val Asp Lys Tyr Phe
465             470             475             480

Asp Cys Tyr Asp Gly Gly Cys Ile Asn Ala Asn Gln Val Ile Val Asn
            485             490             495

Asn Leu Asp Lys Ser Ala Gly Phe Pro Phe Asn Lys Trp Gly Lys Ala
            500             505             510

Arg Leu Tyr Tyr Asp Ser Met Ser Tyr Glu Asp Gln Asp Ala Leu Phe
            515             520             525

Ala Tyr Thr Lys Arg Asn Val Ile Pro Thr Ile Thr Gln Met Asn Leu
    530             535             540

Lys Tyr Ala Ile Ser Ala Lys Asn Arg Ala Arg Thr Val Ala Gly Val
545             550             555             560

Ser Ile Cys Ser Thr Met Thr Asn Arg Gln Phe His Gln Lys Leu Leu
            565             570             575

Lys Ser Ile Ala Ala Thr Arg Gly Ala Thr Val Val Ile Gly Thr Ser
            580             585             590

Lys Phe Tyr Gly Gly Trp His Asn Met Leu Lys Thr Val Tyr Ser Asp
            595             600             605

Val Glu Asn Pro His Leu Met Gly Trp Asp Tyr Pro Lys Cys Asp Arg
    610             615             620

Ala Met Pro Asn Met Leu Arg Ile Met Ala Ser Leu Val Leu Ala Arg
625             630             635             640

Lys His Thr Thr Cys Cys Ser Leu Ser His Arg Phe Tyr Arg Leu Ala
            645             650             655

Asn Glu Cys Ala Gln Val Leu Ser Glu Met Val Met Cys Gly Gly Ser
            660             665             670

Leu Tyr Val Lys Pro Gly Gly Thr Ser Ser Gly Asp Ala Thr Thr Ala
            675             680             685

Tyr Ala Asn Ser Val Phe Asn Ile Cys Gln Ala Val Thr Ala Asn Val
    690             695             700

Asn Ala Leu Leu Ser Thr Asp Gly Asn Lys Ile Ala Asp Lys Tyr Val
705             710             715             720

Arg Asn Leu Gln His Arg Leu Tyr Glu Cys Leu Tyr Arg Asn Arg Asp
            725             730             735

Val Asp Thr Asp Phe Val Asn Glu Phe Tyr Ala Tyr Leu Arg Lys His
            740             745             750

Phe Ser Met Met Ile Leu Ser Asp Asp Ala Val Val Cys Phe Asn Ser
            755             760             765

Thr Tyr Ala Ser Gln Gly Leu Val Ala Ser Ile Lys Asn Phe Lys Ser
    770             775             780

Val Leu Tyr Tyr Gln Asn Asn Val Phe Met Ser Glu Ala Lys Cys Trp
```

-continued

```
785                 790                 795                 800

Thr Glu Thr Asp Leu Thr Lys Gly Pro His Glu Phe Cys Ser Gln His
                805                 810                 815

Thr Met Leu Val Lys Gln Gly Asp Asp Tyr Val Tyr Leu Pro Tyr Pro
                820                 825                 830

Asp Pro Ser Arg Ile Leu Gly Ala Gly Cys Phe Val Asp Asp Ile Val
                835                 840                 845

Lys Thr Asp Gly Thr Leu Met Ile Glu Arg Phe Val Ser Leu Ala Ile
    850                 855                 860

Asp Ala Tyr Pro Leu Thr Lys His Pro Asn Gln Glu Tyr Ala Asp Val
865                 870                 875                 880

Phe His Leu Tyr Leu Gln Tyr Ile Arg Lys Leu His Asp Glu Leu Thr
                885                 890                 895

Gly His Met Leu Asp Met Tyr Ser Val Met Leu Thr Asn Asp Asn Thr
                900                 905                 910

Ser Arg Tyr Trp Glu Pro Glu Phe Tyr Glu Ala Met Tyr Thr Pro His
        915                 920                 925

Thr Val Leu Gln
    930

<210> SEQ ID NO 9
<211> LENGTH: 7
<212> TYPE: PRT
<213> ORGANISM: Severe acute respiratory syndrome-related coronavirus 2
<220> FEATURE:
<223> OTHER INFORMATION: Peptide LYRNRDV (aa 731-737 of SEQ ID NO: 8)

<400> SEQUENCE: 9

Leu Tyr Arg Asn Arg Asp Val
1               5

<210> SEQ ID NO 10
<211> LENGTH: 8
<212> TYPE: PRT
<213> ORGANISM: Severe acute respiratory syndrome-related coronavirus 2
<220> FEATURE:
<223> OTHER INFORMATION: Peptide HRFYRLAN (aa 650-657 of SEQ ID NO: 8)

<400> SEQUENCE: 10

His Arg Phe Tyr Arg Leu Ala Asn
1               5

<210> SEQ ID NO 11
<211> LENGTH: 7
<212> TYPE: PRT
<213> ORGANISM: Artificial Sequence
<220> FEATURE:
<223> OTHER INFORMATION: Control peptide NRKRISN

<400> SEQUENCE: 11

Asn Arg Lys Arg Ile Ser Asn
1               5
```

APTAMERS FOR USE IN THE TREATMENT OF *CORONAVIRIDAE* INFECTIONS

CROSS REFERENCE TO RELATED APPLICATIONS

This application claims priority to PCT/EP2021/059328, filed on Apr. 9, 2021, which claims the benefit of European Application No. 20168929.6, filed on Apr. 9, 2022, European Application No. 20176023.8, filed on May 22, 2020, European Application No. 20180781.5, filed on Jun. 18, 2020, and European Application No. 20204036.6, filed on Oct. 27, 2020, the entire contents of which are incorporated by reference herein.

SEQUENCE LISTING

The instant application contains a Sequence Listing which has been submitted electronically in ASCII format and is hereby incorporated by reference in its entirety. Said ASCII copy, created Oct. 6, 2022, is named SequenceListing.txt and is 16,000 bytes in size.

TECHNICAL FIELD

The present invention relates to new aptamer molecules for use in therapy of infections caused by viruses from the Coronaviridae family, a method of preventing infection caused by viruses from the Coronaviridae family in vitro/ex vivo, a pharmaceutical composition and a kit comprising such aptamer molecules, and the use of aptamer molecules for preventing infection of somatic cells with a virus from the Coronaviridae family. The present invention also relates to affinity molecules binding to specific and newly identified epitopes within a key enzyme of Coronaviridae viruses.

BACKGROUND OF THE INVENTION

The emergence of a novel and highly pathogenic coronavirus (SARS-CoV-2) and its rapid international spread poses a serious global public health emergency. Similar to those infected by other pathogenic Coronavirus strains such as severe acute respiratory syndrome coronavirus (SARS-CoV) in 2003 and Middle East respiratory syndrome coronavirus (MERS-CoV) in 2012, patients infected by SARS-CoV-2 manifest a range of symptoms including dry cough, fever, headache, dyspnea and pneumonia with an estimated mortality rate in the range of 3-5%.

Since the initial outbreak in December of 2019, SARS-CoV-2 has spread to 212 countries, areas and territories worldwide overall. As of Apr. 8, 2020, 1,317,130 infections with the virus have been confirmed globally with 74,304 confirmed deaths of infected patients (https://.who.int/emergencies/diseases/novel-coronavirus-2019).

Currently, various cities and countries across the world are under lockdown to various extents to minimize continued spread, and the WHO has announced a Public Health Emergency of International Concern (PHEIC) duo to the rapid and global dissemination of SARS-CoV-2.

Phylogenetic analysis on the coronavirus genomes has revealed that SARS-CoV-2 is a new member of the *Betacoronavirus* genus, which includes SARS-CoV, MERS-CoV, bat SARS-related coronaviruses (SARSr-CoV), as well as others identified in humans and diverse animal species.

Each coronavirus contains four structural proteins, including spike (S), envelope (E), membrane (M), and nucleocapsid (N) proteins. Among them, the Spike glycoprotein or S protein plays the most important role in viral attachment, fusion and entry, and it serves as the most promising target for development of antibodies, entry inhibitors and vaccines. The S protein mediates viral entry into host cells by first binding to a host receptor through the receptor-binding domain (RBD) in the 51 subunit and then fusing the viral and host membranes through the S2 subunit (Lu, G. et al. *Nature* 500, 227-231 (2013).). Thus, the homotrimeric spike glycoprotein (51 subunit and S2 subunit in each spike monomer) on the virus envelope is used to bind their cellular receptors. Such binding triggers a cascade of events leading to the fusion between cell and viral membranes for cell entry.

SARS-CoV and MERS-CoV RBDs recognize different receptors. SARS-CoV recognizes angiotensin-converting enzyme 2 (ACE2) as its receptor, whereas MERS-CoV recognizes dipeptidyl peptidase 4 (DPP4) as its receptor. Similar to SARS-CoV, SARS-CoV-2 also recognizes ACE2 as its host receptor binding to viral S protein (Zhou, P., et al. *Nature* 579, 270-273 (2020).).

Previous cryo-EM studies of the SARS-CoV Spike and its interaction with the cell receptor ACE2 have shown that binding to ACE2 receptor on the target somatic cell is a critical initial step for the SARS-CoV to enter into target cells. Recent studies also pointed to the important role of ACE2 in mediating entry of SARS-CoV-2 (Walls, A. C. et al. *Cell* S0092-8674(20)30262-2 (2020). https://doi.org/ 10.1016/j.cell.2020.02.058. and Hoffmann, M. et al. *Cell* S0092-8674 (20)30229-4 (2020). https://doi.org/10.1016/ j.cell.2020.02.052).

HeLa cells expressing ACE2 are susceptible to SARS-CoV-2 infection while those lacking the receptor are not. In vitro binding measurements also showed that the SARS-CoV-2 receptor-binding domain (RBD) binds to ACE2 with an affinity in the low nM range, indicating that the RBD is the key functional component within the 51 subunit of the Spike glycoprotein responsible for binding of SARS-CoV-2 by ACE2.

More recently, it could be demonstrated that SARS-CoV2 also uses heparan sulfate as co-factor or cell-attachment factor enabling the subsequent successful ACE-2 mediated cell entry. A preceding contact of the RBD with heparan sulfate may function as a "virus-collector", necessary for subsequent cell-uptake. Here, the positively charged amino-acids of the RBD of SARS-CoV-2 are discussed as potential binding partners to heparan sulfate and heparin (Clausen et al., 2020, *Cell* 183, 1043-1057.e15.).

In summary, the Spike protein of each respective Coronavirus is crucial and relevant for the infectiousness and pathogenicity of the virus. At this stage, there is significant activity in research and development to identify novel and additional agents which are directed against Coronavirus spike proteins and thus able to interfere with the infection process. While antibodies may be developed which target this moiety selectively, it may be even more advantageous to identify (small) molecules which have passed Phase I clinical trials and thus can be safely administered to patients.

In addition, a virus and the viral infection cycle has more vulnerable sites which can theoretically be attacked by a substance. In the case of oligonucleotide-based drugs, also known as aptamers, several such critical sites which are vulnerable to interference by such molecules had been identified and described before. Additional potential target sites for drugs including small molecules, antibody-derived biologics as well as aptamers are enzymes involved in the replication process of RNA viruses. The characterization of such novel target sites and affinity molecules directed against such novel target sites would supplement the tool kit for combatting Coronaviridae infections.

An overview of antivirally active aptamers has been provided by Gonzalez et al. and Zou et al. (González, V. M. et al., 2016. Use of Aptamers as Diagnostics Tools and Antiviral Agents for Human Viruses. Pharmaceuticals (Basel) 9. https://doi.org/10.3390/ph9040078 and Zou et al., 2019. Application of Aptamers in Virus Detection and Antiviral Therapy. Front Microbiol 10, 1462. https://doi.org/10.3389/fmicb.2019.01462).

In fact, anti-Coronaviral therapy has further been reported, based on the isolation of inhibitory RNA and DNA aptamers, respectively, against severe acute respiratory syndrome (SARS) coronavirus NTPase/Helicase. Among such antivirally active aptamers, the anti-influenza aptamer A22 (-AATTAACCCTCACTAAAGGGCTGAGTCT-CAAAACCGCAATACACTGGTTGTATGGTCGAAT AAGTTAA; SEQ ID No. 6) blocking the receptor binding region of hemagglutinin should be mentioned. Besides the virus's cell entry mediator as a target according to the present invention, other virus-target binding sites have also already been identified such as the nucleoprotein of the influenza virus (Negri et al., 2012. Direct Optical Detection of Viral Nucleoprotein Binding to an Anti-Influenza Aptamer. Anal Chem. 2012 Jul. 3; 84(13): 5501-5508.).

Recent publications based on newly raised data from COVID-19 patients suggest or even prove that SARS-CoV-2 can reach the blood stream and various areas of the body, where it appears to cause microthromboses. Such microthrombosis is currently seen as one of the main causes of death of COVID-19 patients (Ackermann M. et al., N Engl J Med. 2020 doi: 10.1056/NEJMoa2015432; Varga Z et al., The Lancet 2020 doi: 10.1016/S0140-6736(20)30937-5.; Wichmann D et al. Annals of Internal Medicine 2020 doi: 10.7326/M20-2003).

Over the course of the pandemic, it has become apparent e.g. in an Italian study that a high percentage of patients of more than 85% exhibit persistent symptoms even after recovering from COVID-19 (Carfi A, Bernabei R, Landi F, Gemelli Against COVID-19 Post-Acute Care Study Group (2020) Persistent Symptoms in Patients After Acute COVID-19. JAMA 324:603-605. https://doi.org/10.1001/jama.2020.12603). Similar results concerning the extent of post-COVID-19 symptoms have been confirmed in a German study that showed more than 75% of their investigated COVID-19 patients exhibiting post-disease symptoms (Puntmann V O, Carerj M L, Wieters I, et al (2020) Outcomes of Cardiovascular Magnetic Resonance Imaging in Patients Recently Recovered From Coronavirus Disease 2019 (COVID-19). JAMA Cardiol. https://doi.org/10.1001/jamacardio.2020.3557.).

The complex of persisting symptoms observed after the active SARS-CoV-2 infection and the disease COVID-19 has subsided is commonly termed Post-COVID syndrome, Long COVID, PASO (Post-Acute Sequelae of SARS-CoV-2 infection), CCS (chronic COVID syndrome) or long-haul COVID.

These symptoms may include one or more neurological disturbances, such as chronic fatigue syndrome, postural orthostatic tachycardia syndrome (PoTS), dysautonomia, transverse myelitis, acute necrotising myelitis, Guillain-Barré syndrome and others, as well as cardiovascular implications, such as myocardial inflammation, arrhythmia, tachycardia, bradycardia, and atrioventricular (AV) block, which may even escalate to cardiac arrest.

Accordingly, new therapeutic agents are required not only for prevention and treatment of active SARS-CoV-2 infections but also for prevention and treatment of symptoms following such infections in the form of Long COVID. Interestingly, a connection was recently implicated between Long COVID and autoimmunity. In this regard, a SARS-CoV-2 triggered autoimmune response was suggested as possible key factor for severity and longevity (Long-COVID) of the disease (Khamsi R 2021, Nature 590(7844): 29-31.).

Any new compounds and compositions may theoretically find use in many clinically relevant applications within a short time frame, including mitigating and curing symptoms caused by Coronaviridae in patients.

Accordingly, it is an object of the present invention to provide new molecules for the use in therapy of a subject suffering from an infection with a virus from the family Coronaviridae.

Furthermore, it is another object of the present invention to provide a method for preventing infection of somatic cells with a virus from the Coronaviridae family.

It is also an object of the present invention to provide a pharmaceutical composition and a kit which may be used against such viral infections.

It is a further object of the present invention to provide a use of novel molecules for preventing infection of somatic cells with a virus from the Coronaviridae family.

In view of the recently recognized relevance of microthrombosis in the course of COVID-19 disease, it is also an object to provide new molecules which are effective against infection with a virus from the family Coronaviridae and at the same time show anticoagulatory effects.

It is further an object of the present invention to provide affinity molecules which are directed against novel target sites within the Coronaviridae replication machinery.

SUMMARY OF THE INVENTION

The aforementioned objects are solved by the aspects of the present invention as specified hereinafter.

According to the first aspect of the present invention, an aptamer is provided for use in therapy of a subject by treating, curing or preventing further progression of infection with a virus from the Coronaviridae family, wherein the aptamer comprises a nucleic acid sequence of SEQ ID No. 1 (GGT TGG TGT GGT TGG) and/or a nucleic acid sequence being at least 80% identical to SEQ ID No. 1.

In a preferred embodiment of the first aspect of the invention, the subject is a mammal, preferably the subject is a human.

In one preferred embodiment of the first aspect of the invention, the infection is caused by a virus from the genus *Betacoronavirus*, preferably from the subgenus Sarbecovirus or Merbecovirus, more preferably by a virus selected from the group comprising MERS-CoV, SARS-CoV and SARS-CoV-2.

In another preferred embodiment of the first aspect of the invention, the infection is caused by a virus from the subgenus Sarbecovirus, preferably from the species Severe acute respiratory syndrome-related coronavirus, even more preferably one of SARS-CoV and SARS-CoV-2

In a specifically preferred embodiment of the first aspect of the invention, the infection is caused by SARS-CoV-2.

In one preferred embodiment of the first aspect of the invention, the aptamer has anticoagulant activity, preferably the aptamer is able to prolong coagulation time measured as partial thromboplastin time (PTT or alternatively aPTT) of human calibration plasma to 60 seconds or more at an aptamer concentration of 0.03 mg/ml and/or the aptamer is able to lower the prothrombin time (Quick value) of human calibration plasma to 40% or less at an aptamer concentration of 0.03 mg/ml.

In another preferred embodiment of the first aspect of the invention, the aptamer selectively interacts with or binds to human thrombin, preferably the $K_D$ value for binding of the aptamer to human thrombin is 1 μM or less.

In a preferred embodiment of the first aspect of the present invention, the aptamer interferes with the infection of somatic cells by selectively interacting with the Spike (S) glycoprotein, preferably with the Receptor-binding domain (RBD) of the Spike (S) glycoprotein, of the virus, more preferably by preventing or interfering with the interaction of the Spike glycoprotein of the virus and the angiotensin-converting enzyme 2 (ACE2) or the dipeptidyl peptidase 4 (DPP4), even more preferably the ACE2, of a subject host cell.

In a more preferred embodiment of the previous embodiment of the first aspect of the present invention, the Receptor-binding domain of the Spike glycoprotein has a sequence of SEQ ID NO: 2 (SARS-CoV-2 Spike RBD) or SEQ ID NO: 3 (SARS-CoV Spike RBD) or SEQ ID NO: 4 (MERS-CoV Spike RBD), preferably wherein the Receptor-binding domain of the Spike glycoprotein has a sequence of SEQ ID NO: 2 or SEQ ID NO: 3, preferably wherein the Spike glycoprotein has a sequence of SEQ ID NO: 2.

In one preferred embodiment of the present invention, the aptamer is administered to the subject by systemic delivery or pulmonary delivery, preferably by pulmonary delivery, more preferably by inhalation.

According to the second aspect of the present invention, an aptamer is provided for use in therapy of a subject by treating, curing or preventing disease symptoms associated with Long COVID in a patient having overcome an infection with a virus from the Coronaviridae family, wherein the aptamer comprises a nucleic acid sequence of SEQ ID No. 1 (GGT TGG TGT GGT TGG) and/or a nucleic acid sequence being at least 80% identical to SEQ ID No. 1.

In a preferred embodiment of the second aspect, the disease symptoms comprise one or more from the group comprising neurological symptoms, such as chronic fatigue syndrome, postural orthostatic tachycardia syndrome (PoTS), dysautonomia, tremor, attention deficit, anomic aphasia, neuropathy, transverse myelitis, acute necrotising myelitis, and Guillain-Barré syndrome, cardiovascular symptoms, such as myocardial inflammation, arrhythmia, tachycardia, bradycardia, hypertension, and atrioventricular (AV) block, dermatological symptoms, such as alopecia and eczema, or gastrointestinal diseases.

In another preferred embodiment of the second aspect of the present invention, the aptamer is used to inhibit the interaction of autoantibodies specific for a G-protein coupled receptor with its target proteins.

In yet another preferred embodiment of the second aspect of the present invention, the aptamer is for use in the treatment of a patient in which autoantibodies against G-protein coupled receptors can be detected.

In one preferred embodiment of the second aspect of the present invention, the patient exhibits functional autoantibodies against G-protein coupled receptors, preferably functional autoantibodies specific for any one of the human G-protein coupled receptor adrenergic alpha-1 receptor, adrenergic beta-2 receptor, endothelin 1 ETA receptor, muscarinic $M_2$ receptor, angiotensin II AT1 receptor, MAS-receptor and/or the nociception receptor, more preferably for any one of the adrenergic beta-2 receptor, muscarinic $M_2$ receptor, angiotensin II AT1 receptor, MAS-receptor, particularly preferably wherein the patient exhibits an antibody pattern comprising functional autoantibodies specific for each of the adrenergic beta-2 receptor, muscarinic $M_2$ receptor, angiotensin II AT1 receptor, and MAS-receptor.

According to the third aspect of the present invention, a method of preventing infection of somatic cells with a virus from the Coronaviridae family by using an aptamer is provided, wherein the method is carried out in vitro/ex vivo and wherein the aptamer comprises a nucleic acid sequence of SEQ ID No. 1 (GGT TGG TGT GGT TGG) and/or a nucleic acid sequence being at least 80% identical to SEQ ID No. 1.

In a preferred embodiment of the third aspect of the present invention, the cell is a mammalian cell, preferably wherein the cell is a human cell.

According to the fourth aspect of the present invention, a pharmaceutical composition is provided comprising an aptamer for use according to the first aspect of the present invention and at least one pharmaceutically acceptable excipient.

In a preferred embodiment of the fourth aspect of the present invention, the pharmaceutical composition for use according to the first aspect is for administration to the subject by systemic delivery or pulmonary delivery, preferably by pulmonary delivery, more preferably by inhalation.

According to the fifth aspect of the present invention, a kit is provided comprising at least one aptamer for use according to the first aspect of the present invention and a container.

According to the sixth aspect of the present invention, the use of the aptamer as defined in the first aspect of the present invention is provided for preventing infection of somatic cells with a virus from the Coronaviridae family, wherein the aptamer is used in vitro/ex vivo.

According to the seventh aspect of the present invention, affinity molecules are provided that specifically bind to a peptide of amino acid sequence Leu-Tyr-Arg-Asn-Arg-Asp-Val (LYRNRDV; SEQ ID NO: 9) and/or His-Arg-Phe-Tyr-Arg-Leu-Ala-Asn (HRFYRLAN; SEQ ID NO: 10) of the RNA-dependent RNA polymerase of the Severe acute respiratory syndrome coronavirus 2.

In a preferred embodiment of the seventh aspect of the present invention, the affinity molecule is a small molecule having a molecular weight of at most 900 Daltons, more preferably the affinity molecule is a small molecule from any one small molecule collection from the group comprising the University of Cincinnati Compound Collection, the DiscoveryProbe™ Bioactive Compound Library Plus from ApexBio Technology LLC, and the SARS-CoV-2 Screening Library from Cayman Chemical.

In another preferred embodiment of the seventh aspect of the present invention, the affinity molecule is a peptide-based compound, more preferably an antibody or a binding fragment thereof.

In one preferred embodiment of the seventh aspect of the present invention, the affinity molecule is an aptamer or oligonucleotide.

In an eighth aspect of the present invention, the affinity molecule of the seventh aspect is provided for use as a medicament.

In a ninth aspect of the present invention, the affinity molecule of the seventh aspect is provided for use in therapy of a subject by treating, curing or preventing further progression of infection with a virus from the Coronaviridae family.

DESCRIPTION OF FIGURES

FIG. 4 shows an ELISA test of the binding of the aptamer of the present invention BC007 (SEQ ID NO: 1) to immobilized human thrombin.

FIG. 5 shows the results of a determination of coagulation inhibition caused by the aptamers BC007 (SEQ ID NO: 1) and AS1411 (SEQ ID NO: 7), respectively, measured as (A) partial thromboplastin time (PTT) and as (B) prothrombin time (Quick) value.

FIG. 10 shows an overview of Long COVID symptoms and accompanying GPCR autoantibodies in patient sera.

FIG. 11 shows the measurement of functionally active autoantibodies which target G-protein coupled receptors from serum of patients suffering from Post-COVID-symptoms in a bioassay. A: positive chronotropic autoantibodies against the beta2-adrenoceptor (beta2-R), the nociceptin receptor (nociceptin-R), the angiotensin II AT1 receptor (AT1), and the alpha1-adrenoceptor (alpha1-R); these measurements were done in the presence of the antagonist Atropine, A779, and BQ123 which block the antibodies that exert a negative chronotropic effect; when pre-incubated with the aptamer BC 007, the functional activity was abolished. Controls were samples of healthy donors. B: negative chronotropic autoantibodies against the MAS-receptor (MAS-R), the muscarinic M2-receptor (M2-R), the endothelin receptor (ETA-R); here, the activity of positive chronotropic acting autoantibodies was blocked by 101118.551, J113397, losartan, and urapidil; when pre-incubated with the aptamer BC 007, the functional activity was abolished. Controls were samples of healthy donors; Neuro*=neurological symptoms; Cardiovasc**=cardiovascular symptoms, n.a.=not applicable, PoTS=postural orthostatic tachycardia syndrome; NOC-$_f$AAB$^§$ =functionally active autoantibody against the nociceptin receptor, β2-$_f$AAB$^§$ =autoantibody targeting the beta1-adrenoceptor, α1-$_f$AAB$^&$=autoantibody targeting the alpha1-adrenoceptor, ETA-$_f$AAB$^+$=autoantibody targeting the endothelin receptor, M2-$_f$AAB$^{%}$=autoantibody targeting the muscarinic receptor, AT1-$_f$AAB$^?$=autoantibody targeting the angiotensin II AT1 receptor, MAS-$_f$AAB$^#$=autoantibody targeting the MAS receptor

DETAILED DESCRIPTION OF THE INVENTION

Figure 1:
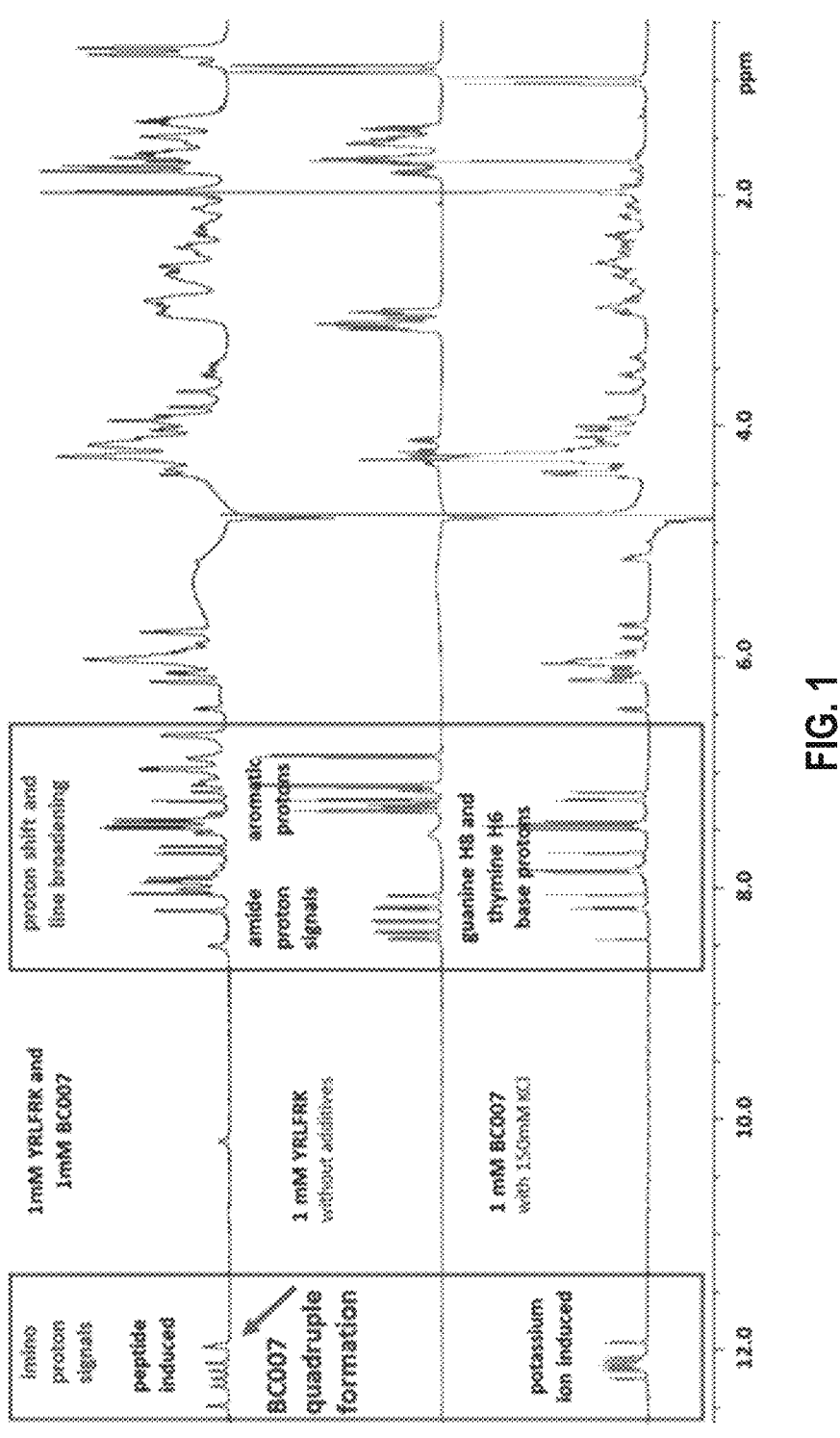
FIG. 1 shows NMR-analysis of quadruplex formation of BC 007 in presence of peptide No. 4 (a 6 aa peptide-sequence of SEQ ID NO: 5; YRLFRK) from the spike protein of SARS-CoV-2; upper spectrum: 1H-NMR spectrum of a 1:1 mixture of BC007 and peptide No. 4 with the sequence YRLFRK; middle spectrum: the spectrum of peptide No. 4 of SEQ ID NO: 5 in pure water; bottom spectrum: spectrum of the quadruplex structure of BC007 in the presence of KCl.

The present invention is based on the identification of novel compounds which are able to selectively interact with the Spike protein of viruses of the Coronaviridae family and thus are expected to interfere with the infection of somatic cells by such viruses. Furthermore, the inventors successfully recognized that specific aptamer molecules are able to inhibit the infectious activity and replication of such viruses in human cells.

The present inventors intensively studied the interaction of the aptamer of SEQ ID NO: 1, which is also commonly referred to as thrombin-binding aptamer or BC007, with several binding partners, such as thrombin. While investigating the specificities of the interaction between BC007 and thrombin using NMR technology, it could be detected that not the entire, full-length thrombin-molecule was required for strong binding to BC007 as evidenced by adoption of an NMR-detectable quadruplex structure by BC007.

In fact, much shorter peptide sequences taken from the binding moiety were recognized to lead to the same results (data not shown). In fact, it became clear that peptides taken from full-length thrombin that cause quadruplex folds of BC007 consist of or possess sequence motifs containing several amino acids with side chains having positive charges, preferably of arginine. These peptides could represent solvent-facing surfaces due to their positive charge which may then selectively be bound by the claimed aptamers in thrombin as well as in other proteins such as Spike proteins of viruses from the Coronaviridae family.

Faced with the problems caused by the current outbreak of SARS-CoV-2 and other Coronavirus-related infections, the present inventors considered if the claimed aptamer molecules could potentially have a function as agents against Coronavirus infections.

Surprisingly, the inventors learned that Spike proteins of different Coronavirus strains, in particular sequences belonging to the receptor-binding domains thereof, possess sequence motifs containing several amino acids with side chains having positive charges, such as Arginine-rich-clusters (cf. Hoffmann et al., 2020, supra).

Based on this information together with substantial experience from studying the interaction of specific aptamers with thrombin, the inventors successfully identified representative clusters of positively charged amino acids and Arginine-rich sequence sections (e.g. clusters) within the receptor-binding domain of the virus Spike protein of SARS-CoV-2 as well as previously unknown target peptides within the RNA-dependent RNA polymerase of Coronaviridae viruses.

Peptide No. 4 (with the amino acid sequence YRLFRK; SEQ ID NO: 5) which is part of the receptor-binding domain of the S1 subunit of the Spike protein of SARS-CoV-2 was selected as a representative peptide for binding studies with BC007. It has surprisingly been observed that there is in fact strong interaction between Peptide No. 4 and BC007 which leads to BC007 adapting a quadruplex fold (see FIGS. 1 and 2 and Example 1 in the Examples section below).

Such strong interaction is highly plausible and likely to persist in the full-length molecule, the whole Spike protein as well as entire virus particles, in which the Spike protein is responsible for infectivity and pathogenicity of viruses of the Coronaviridae family. Also, based on the presence of clusters of positively charged amino acids within the Spike protein of other virus strains from the Coronaviridae family, it is plausible that the present invention is useful against other such viruses as well.

Departing from this evidence for strong interaction of the aptamer of the present invention with a Spike sequence motif of SARS-CoV-2, the inventor proceeded to carry out an analysis of the inhibitory activity of the inventive aptamer on SARS-CoV-2 infecting human cells.

Surprisingly, the aptamer of the present invention not only demonstrated a very efficient inhibition of the viral activity of SARS-CoV-2 but actually appeared to surpass other antiviral agents currently discussed as potential therapeutic options for COVID-19 (see Example 2).

These results evidently reflect the therapeutic effect on which the therapeutic application of using the inventive aptamer in treating, curing or preventing an infection with viruses of the Coronaviridae family is based.

In addition to the observed effects, it has previously been reported that G-quadruple oligonucleotide-structures cause the development of anti-viral effects in e.g. HIV infection, not only by inhibiting HIV entry into host cells (ISIS5320) but also inhibiting HIV integrase itself (T30177 or AR177, the first integrase inhibitor in clinical trials) (for review see Roxo, C., et al., 2019. G-Quadruplex-Forming Aptamers-Characteristics, Applications, and Perspectives. Molecules 24. https://doi.org/10.3390/molecules24203781).

HIV is, just like SARS-CoV-2 and other Coronaviridae viruses, an ssRNA virus, which means that virus replication steps are comparable. It is, therefore, highly probable that the claimed aptamers which may adopt a G-quadruplex-like fold upon interaction with binding partners might also be able to inhibit the SARS-CoV-2 integrase or other vulnerable sites in addition to a direct interaction with the Spike protein.

Furthermore, recent data indicating a significant relevance of microthrombosis in deaths of patients suffering from COVID-19, molecules having antithrombotic and anticoagulatory effects are studied in the context of Coronaviridae infections. The ability of the presently claimed aptamer molecules to combat the infection with a virus from the family Coronaviridae and at the same time show anticoagulatory effects makes the present invention even more suitable for use against COVID-19 and other Coronaviridae-associated diseases.

This is a particular advantage of the aptamer of the present invention over other aptamers recently suggested as therapeutic agents against COVID-19, such as the aptamer AS1411 (SEQ ID NO: 7). Such comparative aptamers are devoid of any antithrombotic or anticoagulatory effects and thus lack the dual mode of attack of the present invention. AS1411 was originally developed as a synthetic DNA molecule that binds a protein called nucleolin found on the surface of cells. Based on this activity, it has been previously studied as an experimental drug for cancer treatment.

According to one aspect of the present invention, an aptamer is provided for use in therapy of a subject by treating, curing or preventing further progression of infection with a virus from the Coronaviridae family, wherein the aptamer comprises a nucleic acid sequence of SEQ ID No. 1 (GGT TGG TGT GGT TGG) and/or a nucleic acid sequence being at least 80% identical to SEQ ID No. 1.

Within the present invention, a use in treating of an infection with a virus shall also mean that the first infection of a subject may be prevented by the aptamer for use according to the invention. In addition and more importantly, the aptamer for use according to the present invention shall be used in treating, curing or preventing further progression of infection in subjects that have been identified as being infected with a virus from the Coronaviridae family.

With regard to the new findings of Clausen et al., 2020 as discussed above, it is further likely and plausible that the aptamer of SEQ ID No. 1 might also compete with a heparin binding motive of RBD. Said aptamer has already been reported to selectively interact with the heparin binding motive of thrombin (exosite 2; cf. Padmanabhan and Tulinsky, 1996 *Acta Crystallogr D Biol Crystallogr* 52:272-282) besides its well known and investigated binding onto exosite 1, the fibrinogen binding site of thrombin. Due to an increased presence of negatively charged amino acids at such heparin binding sites, binding of SEQ ID No. 1 at the heparin binding sites of the RBD of SARS-CoV-2 in analogy to the known binding to the heparin binding motive of thrombin appears plausible.

According to one embodiment of the present invention, the aptamer further interferes with the infection of somatic cells by selectively interacting with the cellular heparan sulfate of a subject host cell.

According to a preferred embodiment of the present invention, the subject in which the viral infection should be treated, cured or further progression thereof prevented is a vertebrate, more preferably the subject is a mammal. Within the meaning of the present invention, the group of mammals includes but is not limited to rats, mice, ferrets, rabbits, cats, dogs, horses, cattle, cows, pigs, sheep, non-human primates and humans. Most preferably, the subject is a human.

In a preferred embodiment of the present invention, the aptamer of the present invention disclosed and described herein comprises a nucleic acid sequence of SEQ ID No. 1 (GGT TGG TGT GGT TGG) and/or a nucleic acid sequence being at least 80% identical to SEQ ID No. 1. In another more preferred embodiment, the aptamer comprises the nucleic acid sequence of SEQ ID No. 1 (GGT TGG TGT GGT TGG), in particular the aptamer consists of the nucleic acid sequence of SEQ ID No. 1 (GGT TGG TGT GGT TGG).

The determination of percent identity between two sequences is accomplished according to the present invention by using the mathematical algorithm of Karlin and Altschul (Proc. Natl. Acad. Sci. USA (1993) 90: 5873-5877). Such an algorithm is the basis of the BLASTN and BLASTP programs of Altschul et al. (J. Mol. Biol. (1990) 215: 403-410). BLAST nucleotide searches are performed with the BLASTN program. To obtain gapped alignments for comparative purposes, Gapped BLAST is utilized as described by Altschul et al. (Nucleic Acids Res. (1997) 25: 3389-3402). When utilizing BLAST and Gapped BLAST programs, the default parameters of the respective programs are used.

According to a more preferred embodiment of the present invention, aptamer sequences form part of the invention which consist of or comprise a nucleic acid sequence being at least 85% identical to the individualized aptamer sequences which are disclosed herein, even more preferably at least 90% identical, particularly preferably at least 95% identical.

For the purpose of this invention, the term "aptamer" refers to an oligonucleotide that binds specifically and with high affinity to a target molecule. Under defined conditions, aptamers may fold into a specific three dimensional structure. In one preferred embodiment of the present invention, the claimed aptamers interact specifically and with high affinity with the target sequence.

According to a preferred embodiment, the aptamers interact with a sequence within the Spike glycoprotein of a virus from the Coronaviridae family, preferably to a sequence within the S1 subunit, more preferably to a sequence within the receptor binding domain thereof. According to one embodiment of the present invention, the aptamer binds to a region within the virus sequence which has two or more positively charged amino acids, more preferably arginine, within a stretch of seven amino acids.

The aptamer of the invention comprises or consists of a sequence of nucleic acid molecules, the nucleotides. According to a preferred embodiment, the aptamer of the invention consists of a nucleotide sequence as defined herein.

The aptamer of the invention preferably comprises unmodified and/or modified D- and/or L-nucleotides. According to the common one letter code of nucleic acid bases "C" or stands for cytosine, "A" or stands for adenine, "G" or stands for guanine, and "T" or stands for thymine if the nucleotide sequence is a DNA sequence and "T" or stands for a uracil nucleotide if the nucleotide sequence is a RNA sequence. If not indicated below to the contrary, the term "nucleotide" shall refer to ribonucleotides and desoxyribonucleotides.

The aptamer of the invention can comprise or consist of a DNA- or an RNA-nucleotide sequence and, thus, can be referred to as DNA-aptamer or RNA-aptamer, respectively. It is understood that, if the aptamer of the invention comprises an RNA-nucleotide sequence, within the sequence motifs specified throughout the present invention "T" stands for uracil.

For the sake of conciseness throughout the present invention, reference is made solely to explicit DNA-nucleotide sequences. However, it is understood that the respective RNA-nucleotide sequences are also comprised by the present invention.

According to one embodiment, the use of DNA-aptamers is preferred. DNA-aptamers are usually more stable in plasma than RNA-aptamers. However, according to an alternative embodiment, RNA-aptamers are preferred. According to another embodiment, single strand nucleotide sequences are preferred. According to another alternative embodiment, double strand nucleotide sequences are preferred.

The aptamers of the invention may comprise a nucleotide sequence containing 2'-modified nucleotides, e.g. 2'-fluoro-, 2'-methoxy-, 2'-methoxyethyl- and/or 2'-amino-modified nucleotides. The aptamer of the invention may also comprise a mixture of desoxyribonucleotides, modified desoxyribonucleotides, ribonucleotides and/or modified ribonucleotides. Respectively, the terms "2'-fluoro-modified nucleotide", "2'-methoxy-modified nucleotide", "2'-methoxyethylmodified nucleotide" and/or "2-amino-modified nucleotide" refer to modified ribonucleotides and modified desoxyribonucleotides.

The aptamer of the invention may comprise modifications. Such modifications encompass e.g. alkylation, i.e. methylation, arylation or acetylation of at least one nucleotide, the inclusion of enantiomers and/or the fusion of aptamers with one or more other nucleotides or nucleic acid sequences. Such modifications may comprise e.g. 5'- and/or 3'-PEG- or 5'- and/or 3'-CAP-modifications. Alternatively or in addition, the aptamer of the invention may comprise modified nucleotides, preferably selected from locked-nucleic acids, 2'-fluoro-, 2'-methoxy- and/or 2'-amino-modified nucleotides.

Locked nucleic acids (LNA) represent analogons of the respective RNA nucleotides wherein the conformation has been fixed. Oligonucleotides of locked nucleic acids comprise one or more bicyclic ribonucleosides, wherein the 2'-OH group is connected with the $C_4$-carbon atom via a methylen group. Locked nucleic acids exhibit an improved stability versus nucleases compared to the respective unmodified RNA-aptamer counterparts. Also the hybridization properties are improved which allows for an enhancement of affinity and specificity of the aptamer.

Another preferred modification is the addition of a so called 3'-CAP-, a 5'-CAP-structure and/or of a modified guanosin-nucleotide (e.g. 7-methyl-guanosin) to the 3'- and/or 5'-end of the aptamer. Such a modification of the 3'-and/or 5'-end has the effect that the aptamer is protected from a fast degradation by nucleases.

Alternatively or in addition, the aptamer of the invention can exhibit a pegylated 3' or 5'-end. A 3'- or 5'-PEG modification comprises the addition of at least one polyethylene glycol (PEG) unit, preferably the PEG group comprises 1 to 900 ethylene groups, more preferably from 1 to 450 ethylene groups. In a preferred embodiment, the aptamer comprises linear PEG units with HO—(CH$_2$CH$_2$O)$_n$—H, wherein n is an integer of 1 to 900, preferably n is an integer of 1 to 450.

The aptamer of the invention can be wholly or in part configured as a peptide nucleic acid (PNA). The aptamers according to the present invention may further be modified as described in Keefe A D et al., Nat Rev Drug Discov. 2010 July; 9(7):537-50 or in Mayer G, Angew Chem Int Ed Engl. 2009; 48(15):2672-89 or in Mayer, G. and Famulok M., Pharmazie in unserer Zeit 2007; 36: 432-436.

The term "oligonucleotide" generally refers to a polynucleoside comprising a plurality of linked nucleoside units. Such oligonucleotides can be obtained from existing nucleic acid sources, including genomic or cDNA, but are preferably produced by synthetic methods. In preferred embodiments each nucleoside unit can encompass various chemical modifications and substitutions as compared to wild-type oligonucleotides, including but not limited to modified nucleoside base and/or modified sugar unit.

Examples of chemical modifications are known to the person skilled in the art and are described, for example, in Uhlmann, E. et al. (1990) Chem. Rev. 90:543; "Protocols for Oligonucleotides and Analogs" Synthesis and Properties & Synthesis and Analytical Techniques, S. Agrawal, Ed, Humana Press, Totowa, USA 1993; and Hunziker, J. et al. (1995) Mod. Syn. Methods 7:331-417; and Crooke, S. et al. (1996) Ann. Rev. Pharm. Tox. 36:107-129.

The nucleoside residues can be coupled to each other by any of the numerous known internucleoside linkages, inter alia to improve stability of the oligonucleotides against enzymatic degradation, e.g. by nucleases. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages.

The term "oligonucleotide" also encompasses poly-nucleosides having one or more stereospecific internucleo-side linkage (e.g., (Rr)- or (Sr)-phosphorothioate, alkylphos-phonate, or phosphotriester linkages). As used herein, the terms "oligonucleotide" and "dinucleotide" are expressly intended to include polynucleosides and dinucleosides hav-ing any such internucleoside linkage, whether or not the linkage comprises a phosphate group. In certain preferred embodiments, these internucleoside linkages may be phos-phodiester, phosphorothioate or phosphorodithioate link-ages or combinations thereof, more preferably the inter-nucleoside linkages are phosphorothioate.

Further, the aptamers may be encapsulated in suitable vehicles to protect their structural integrity as well as to promote their delivery inside cells. Preferred vehicles include liposomes, lipid vesicles, microparticles, and the like.

One advantage of modifying the aptamer of the invention by one of the ways mentioned above is that the aptamer can be stabilized against detrimental influences like e.g. nucle-ases present in the environment wherein the aptamer is used. Said modifications are also suitable to adapt the pharmaco-logical properties of the aptamer. The modifications prefer-ably do not alter the affinity or specificity of the aptamer.

The aptamer of the invention may also be conjugated to a carrier molecule and/or to a reporter molecule. Carrier molecules comprise such molecules that, when conjugated to the aptamer, prolong the plasma half-life of the conju-gated aptamer in human plasma, e.g. by enhancing the stability and/or by affecting the excretion rate. One example of a suitable carrier molecule is PEG.

Reporter molecules comprise molecules that allow for the detection of the conjugated aptamer. Examples of such reporter molecules are GFP, biotin, cholesterol, dyes like e.g. fluorescence dyes, electrochemically active reporter molecules and/or compounds comprising radioactive resi-dues, in particular radionuclides suitable for PET (positron emission tomography) detection like e.g. $^{18}F$, $^{11}C$, $^{13}N$, $^{15}O$, $^{82}Rb$ or $^{68}Ga$. The skilled person is well aware of suitable carrier and reporter molecules and of ways of how to conjugate them to the aptamer of the invention.

In one preferred embodiment of the first aspect of the invention, the aptamer of the invention has anticoagulant activity. Anticoagulant activity may preferably mean anti-thrombotic activity and preferably be understood as prevent-ing or reducing microthromboses.

More preferably the aptamer of the invention is able to prolong coagulation time measured as partial thromboplas-tin time (PTT or alternatively aPTT) of human calibration plasma to 60 seconds or more at an aptamer concentration of 0.03 mg/ml. According to one embodiment of the present invention, the aptamer of the invention is able to prolong coagulation time measured as partial thromboplastin time of human calibration plasma to 40 seconds or more, more preferably to 50 seconds or more at an aptamer concentra-tion of 0.03 mg/ml. According to one preferred embodiment, the aptamer of the present invention prolongs partial throm-boplastin time of human calibration plasma more than aptamer AS1411 (SEQ ID NO: 7).

Also more preferably, the aptamer is able to lower the prothrombin time (Quick value) of human calibration plasma to 40% or less at an aptamer concentration of 0.03 mg/ml. According to one embodiment of the present inven-tion, the aptamer of the invention is able to lower the prothrombin time (Quick value) of human calibration plasma to 80% or less, more preferably to 70% or less, even more preferably to 60% or less, particularly preferably to 50% or less at an aptamer concentration of 0.03 mg/ml. According to one preferred embodiment, the aptamer of the present invention lowers the prothrombin time (Quick value) of human calibration plasma more than aptamer AS1411 (SEQ ID NO: 7).

According to one preferred embodiment, the PTT time is assessed by using the test described in the Examples section hereinbelow. Alternatively preferably, the PTT time and/or the Quick value is assessed as commonly known in the art. As calibration plasma, any human reference plasma of a healthy individuum may be used, preferably HemosIL human calibration plasma (Instrumentation Laboratory, Werfen) is employed.

In another preferred embodiment of the first aspect of the invention, the aptamer selectively interacts with or binds to human thrombin, preferably the $K_D$ value for binding of the aptamer to human thrombin is 1 µM or less, more preferably the $K_D$ value is 100 nM or less, even more preferably the $K_D$ value is 10 nM or less. $K_D$ values may preferably be determined using a dilution series of human thrombin (rang-ing between 1 µM and 1000 nM) in the dot blot binding assay and fitting an equation describing a 1:1 NA:protein complex to the resulting data (fraction aptamer bound=amplitude*([Thrombin]/($K_D$+[Thrombin])) (Ka-leidaGraph v. 3.51, Synergy Software, Reading, Pa.).

Within the present invention, selective binding or inter-action or specific binding or interaction between two mol-ecules may preferably mean that the two cited molecules bind or interact with an at least 10-fold, more preferably at least 50-fold, particularly preferably at least 100-fold increased affinity compared to unrelated, non-interacting or non-binding molecules as binding partners.

The aptamers of the present invention are useful for the treatment of infections with virus strains from the Corona-viridae family. In the context of the present invention, the aptamers are considered to be useful for human subjects as well as for animal subjects. According to one embodiment, the aptamers are for use in human subjects. According to another embodiment, the aptamers are for use in animal subjects.

By inhibiting infection with a Coronavirus, the potentially negative effects of Coronavirus infection are neutralized and diminished and any disease symptom may be abolished or reduced to normal levels. As a consequence, the extent and gravity of a disease caused or associated with Coronavirus infection may be significantly reduced. Thus, the present invention provides aptamers that are suitable for use in treatment of diseases or symptoms associated with Corona-virus infection.

According to another embodiment of the present inven-tion, a method of preventing infection of somatic cells with a virus from the Coronaviridae family is provided by using an aptamer according to the present invention. In one preferred embodiment, the method of preventing infection encompasses treating, curing or preventing progression of infection with a virus from the Coronaviridae family in a subject.

In a preferred embodiment of the present invention, the method is carried out in vitro/ex vivo. More preferably, the cell to be contacted with an aptamer according to the method of the present invention does not form part of a whole living organism. In one embodiment, the cell to be contacted may be cultured in cell culture. Such cultures of individual or groups of cells may be carried out as usually done in the art.

In another preferred embodiment of the method of the present invention, the method may be carried out in vivo and/or on cells which form part of a whole living organism. According to this embodiment, the cells, tissue or organ to be contacted has/have previously been diagnosed as being infected with a virus from the Coronaviridae family. Preferably, the cells to be treated according to the present invention belong to the gastrointestinal or respiratory tracts, more preferably to the respiratory tract, more preferably lung cells are treated.

The present invention is also directed to an aptamer for use in therapy of a subject by treating, curing or preventing disease symptoms associated with long COVID in a patient having overcome an infection with a virus from the Coronaviridae family, wherein the aptamer comprises a nucleic acid sequence of SEQ ID No. 1 (GGT TGG TGT GGT TGG) and/or a nucleic acid sequence being at least 80% identical to SEQ ID No. 1.

Long COVID is a condition or a complex of symptoms which has been observed in patients which have overcome an infection with a virus from the Coronaviridae family. While the complex of symptoms associated therewith is still under examination, it becomes more and more evident that symptoms prevail even after disappearance of symptoms of an active infection.

Based on experimental data also included herein, it became evident that numerous of these observed symptoms in patients having endured an active SARS-CoV-2 infection have an association with the presence of functional autoantibodies (FIG. 10). Since it was previously demonstrated that the aptamers of the present invention have inhibitory activity against such functional autoantibodies (also demonstrated in FIG. 11 herein), the inventive aptamers can be assumed to have activity against such symptoms grouped together as Long COVID.

In any case, the symptoms summarized as Long COVID herein are considered to be late effects or delayed effects of an infection with Coronaviridae such as SARS-CoV-2. In this regard, the special effects of the aptamers of the invention on Long COVID may be seen as part of treating infection with a virus from the Coronaviridae family, such as SARS-CoV-2, as described and claimed herein.

In one embodiment, the disease symptoms comprise one or more from the group comprising neurological symptoms, such as chronic fatigue syndrome, postural orthostatic tachycardia syndrome (PoTS), dysautonomia, tremor, attention deficit, anomic aphasia, neuropathy, transverse myelitis, acute necrotising myelitis, and Guillain-Barré syndrome, cardiovascular symptoms, such as myocardial inflammation, arrhythmia, tachycardia, bradycardia, hypertension, and atrioventricular (AV) block, dermatological symptoms, such as alopecia and eczema, or gastrointestinal diseases.

Preferably, the aptamer is used to inhibit the interaction of autoantibodies specific for a G-protein coupled receptor with its target proteins. Also preferably, the aptamer is for use in the treatment of a patient in which autoantibodies against G-protein coupled receptors can be detected.

In one embodiment of the present invention, the patient to be treated exhibits functional autoantibodies against G-protein coupled receptors, preferably functional autoantibodies specific for any one of the human G-protein coupled receptor adrenergic alpha-1 receptor, adrenergic beta-2 receptor, endothelin 1 ETA receptor, muscarinic M2 receptor, angiotensin II AT1 receptor, MAS-receptor and/or the nociception receptor, more preferably for any one of the adrenergic beta-2 receptor, muscarinic M2 receptor, angiotensin II AT1 receptor, MAS-receptor, particularly preferably wherein the patient exhibits an antibody pattern comprising functional autoantibodies specific for each of the adrenergic beta-2 receptor, muscarinic M2 receptor, angiotensin II AT1 receptor, and MAS-receptor.

The present invention is also directed to a pharmaceutical composition comprising at least one aptamer of the invention and, optionally, at least one pharmaceutically acceptable excipient. The invention is also directed to a pharmaceutical composition comprising an aptamer of the invention or a mixture of different aptamers of the invention and a pharmaceutically acceptable excipient like e.g. a suitable carrier or diluent.

Preferably, the aptamer of the invention constitutes an active ingredient of the pharmaceutical composition and/or is present in an effective amount. The term "effective amount" denotes an amount of the aptamer of the invention having a prophylactically, diagnostically or therapeutically relevant effect on a disease or pathological condition. A prophylactic effect prevents the outbreak of a disease. A therapeutically relevant effect relieves to some extent one or more symptoms of a disease or returns to normal either partially or completely one or more physiological or biochemical parameters associated with or causative of the disease or pathological conditions.

The respective amount for administering the aptamer of the invention is sufficiently high in order to achieve the desired prophylactic, diagnostic or therapeutic effect. It will be understood by the skilled person that the specific dose level, frequency and period of administration to any particular mammal will depend upon a variety of factors including the activity of the specific components employed, the age, body weight, general health, sex, diet, time of administration, route of administration, drug combination, and the severity of the specific therapy. Using well-known means and methods, the exact amount can be determined by one of skill in the art as a matter of routine experimentation.

According to one embodiment of the pharmaceutical composition of the invention, at least 20% of the total aptamer content is made of an aptamer of the invention, preferably at least 50%, more preferably at least 75%, most preferable at least 95%.

When used for therapy, the pharmaceutical composition will generally be administered as a formulation optionally in association with one or more pharmaceutically acceptable excipients. The term "excipient" is used herein to describe any ingredient other than the aptamer of the invention. The choice of excipient will to a large extent depend on the particular mode of administration. Excipients can be suitable carriers and/or diluents.

The pharmaceutical composition of the invention may preferably be administered orally or intravenously. According to one preferred embodiment, the pharmaceutical composition is administered by inhalation. According to an alternative embodiment, the pharmaceutical composition is administered intravenously.

According to a preferred embodiment, the pharmaceutical composition is administered to the subject by systemic delivery or pulmonary delivery, preferably by pulmonary delivery, more preferably by inhalation. The pharmaceutical composition to be administered by inhalation may preferably be in the form of a powder or a spray.

For administration to human patients, the total daily dose of the aptamer of the invention and/or the pharmaceutical composition of the invention is typically in the range 0.001 mg to 8000 mg depending, of course, on the mode of administration. For example, an intravenous daily dose may only require from 0.001 mg to 40 mg. The total daily dose may be administered in single or divided doses and may, at the physician's discretion, fall outside of the typical range given herein.

These dosages are based on an average human subject having a weight of about 75 kg to 80 kg. The physician will readily be able to determine doses for subjects whose weight falls outside this range, such as infants and the elderly.

In the context of the present invention, the aptamer may preferably be administered in combination with one or more vaccines, antigens, antibodies, cytotoxic agents, allergens, antibiotics, antisense oligonucleotides, TLR antagonist, peptides, proteins, gene therapy vectors, DNA vaccines, adjuvants, kinase inhibitors, T-cell therapeutics or sulphated polyglycerols or similar sulphated polymers.

The present invention also encompasses a kit comprising an aptamer of the invention, a container and optionally written instructions for use and/or with means for administration.

For treatment of a disease caused or associated with an infection with a Coronavirus, irrespective of the route of administration, the aptamer of the invention is administered at an overall daily dose per treatment cycle of not more than 150 mg/kg body weight, preferably of not more than 20 mg/kg body weight, more preferably of not more than 10 mg/kg body weight, even more preferably selected from the range of 1 µg/kg to 20 mg/kg body weight, most preferably selected from a range of 0.01 to 10 mg/kg body weight. In a preferred embodiment of the present invention, the aptamer is administered in multiple separate dosage steps over the course of one day, preferably between 2 and 6 times per day, for example 4 times a day. The aptamer may be administered in four doses of 1900 mg each per day.

According to one aspect of the present invention, the use of the aptamer as defined herein is provided for preventing infection of somatic cells with a virus from the Coronaviridae family. In a preferred embodiment of the present invention, the aptamer may be used in vitro/ex vivo. In an alternative preferred embodiment, the aptamer may be used in vivo.

The manufacturing or mass production of aptamers of the invention is well known in the art and represents a mere routine activity.

According to one aspect of the present invention, affinity molecules are provided that specifically bind to a peptide of amino acid sequence Leu-Tyr-Arg-Asn-Arg-Asp-Val (LYRNRDV; SEQ ID NO: 9) and/or His-Arg-Phe-Tyr-Arg-Leu-Ala-Asn (HRFYRLAN; SEQ ID NO: 10) of the RNA-dependent RNA polymerase of the Severe acute respiratory syndrome coronavirus 2 (SEQ ID NO: 8).

Within the present invention, an affinity molecule may be any molecule with high affinity to a given target, e.g. to the peptides of SEQ ID NO: 9 or 10. Binding with high affinity preferably means binding to said target epitopes with an at least 10-fold, preferably at least 50-fold, more preferably at least 100-fold increased affinity compared to unrelated epitopes, proteins or protein regions.

In additional studies carried out by the inventors, it was surprisingly found that the claimed aptamer specifically interacts and binds to two previously unknown, distinct epitopes of the enzyme RNA-dependent RNA polymerase of SARS-CoV-2 (SEQ ID NO: 8; NCBI Reference Sequence Accession Number: YP_009725307.1). By way of NMR studies as well as isothermal titration calorimetry, selective interaction between the aptamer of the present invention and said epitopes of the RNA-dependent RNA polymerase have been conclusively shown (see FIGS. 6 and 7). The defined peptide stretches of this enzyme against which specific binding was observed are amino acids 731 to 737 (LYRNRDV; SEQ ID NO: 9) and amino acids 650 to 657 (HRFYRLAN; SEQ ID NO: 10).

Equivalent target sequences have also been identified in the sequence of RNA-dependent RNA polymerase from another member of the Coronaviridae family, SARS-CoV (data not shown). It is known from the prior art that the sequences of RNA-dependent RNA polymerases share very high amino acid sequence identity within the Coronaviridae family, but has very low sequence similarity to other viral RNA-dependent RNA polymerases and Reverse Transcriptases (cf., for example, Xu X et al. (2003) Molecular model of SARS coronavirus polymerase: implications for biochemical functions and drug design. *Nucleic Acids Res* 31:7117-7130, page 7118, right-hand column, 1$^{st}$ full paragraph, 2$^{nd}$ sentence). Therefore, it can be plausibly assumed that equivalent target sequences are also present in the RNA-dependent RNA polymerase of other viruses of the Coronaviridae family.

Such strong interaction as observed in NMR studies is also in this case highly plausible and likely to persist in the full-length molecule as well as in active viruses of the Coronaviridae family. In fact, the additional activity of the claimed aptamer against the Spike protein as well as against the viral RNA-dependent RNA polymerase could explain the superior results observed in the cell culture assay in comparison to known drugs.

While it was previously reported that antiviral agents active against Coronaviridae such as Remdesivir and Galidesivir may interact with sequences within the RNA-dependent RNA polymerase (cf. Wang Y, Anirudhan V, Du R, Cui Q, and Rong L (2020) RNA-dependent RNA polymerase of SARS-CoV-2 as a therapeutic target. *J Med Virol*, doi: 10.1002/jmv.26264. for studies with Galidesivir and the identification of amino acids Thr455, Arg553, Lys621, Arg624, Asp452, Ala554, Asp623, Asn691, Ser759, Asp760 as target amino acids, and Wu C, Liu Y, Yang Y, Zhang P, Zhong W, Wang Y, Wang Q, Xu Y, Li M, Li X, Zheng M, Chen L, and Li H (2020) Analysis of therapeutic targets for SARS-CoV-2 and discovery of potential drugs by computational methods. *Acta Pharm Sin B, doi:* 10.1016/j.apsb.2020.02.008. for studies with Remdesivir and the identification of amino acids Asn 497, Arg 569, Asp 684, Leu 576, Ala 685, Tyr 687 as target amino acids), the reported sequences are distinct from and unrelated to the peptide stretches identified by the present inventors.

The target enzyme RNA-dependent RNA polymerase is a key component of the viral replication machinery of Coronaviridae viruses. It will be apparent to the skilled person that specific binding of or to such an enzyme will at least interfere with, impair or even inhibit correct and efficient replication of viral RNA of the RNA viruses of the Coronaviridae family. In this way, the infectivity of the virus will be reduced due to an impact on the life cycle of the virus in its host.

The identification of novel epitopes of said key enzyme is a significant contribution to the technical field, since it will allow the generation and identification of additional binding partners also leading to interference with or inhibition of viral replication. Also, since the newly identified epitopes are distinct from any epitopes of said key enzyme previously known as suitable binding sites for affinity molecules, any affinity molecule binding thereto will at least act to supplement the inhibitory action provided by any other molecule specifically binding to RNA-dependent RNA polymerase.

It was additionally recognized and demonstrated that the newly identified epitopes are positioned towards the outside of the enzyme, thus facing the solvent and being easily accessible for specific interaction or binding (data not shown). It should also be mentioned that aptamer binders are in most cases able to interfere with the functionality of their target proteins and are even deliberately expressed for this purpose in vivo (Ulrich H (2005) DNA and RNA aptamers as modulators of protein function. *Medicinal Chemistry* (*Shariqah* (*United Arab Emirates*)) 1:199-208.).

Surprisingly, the aptamer of the present invention not only demonstrated a very efficient inhibition of the viral activity of SARS-CoV-2 but actually appeared to surpass other antiviral agents currently discussed as potential therapeutic options for COVID-19 (see Example 2). This may be due to the dual action on the virus infection process as well as on its replication in the host.

By providing new epitopes of this key enzyme which is crucial for the replication cycle of the virus, the skilled person will be able to identify, raise or generate additional small molecules, antibodies or antibody-derived biologics, or oligonucleotides/aptamers with affinity to said newly identified epitopes by using standard procedures as commonly known in the art.

In a preferred embodiment of the sixth aspect of the present invention, the affinity molecule is a small molecule having a molecular weight of at most 900 Daltons. Preferably the affinity molecule is a small molecule from any one small molecule collection from the group comprising the University of Cincinnati Compound Collection, the DiscoveryProbe™ Bioactive Compound Library Plus from ApexBio Technology LLC, and the SARS-CoV-2 Screening Library from Cayman Chemical.

According to one preferred embodiment of the present invention, the affinity molecule is a small molecule present in the ZINC 15 database (Sterling T and Irwin J J, *Journal of Chemical Information and Modeling* 2015 55 (11), 2324-2337; DOI: 10.1021/acs.jcim.5b00559).

Alternatively preferably, the affinity molecule is found to have potential activity against at least one viral target, more preferably at least two viral targets according to the disclosure of Kowalewski J and Ray A (2020), *Heliyon*. 6. e04639. 10.1016/j.heliyon.2020.e04639.

With respect to COVID-19 inhibition, previous publications already screened existing drug or small molecule libraries and checked for possible interaction/binding with proteins crucial for SARS-CoV-2 infection or replication, exploiting inter alia appropriate in silico methods (computer programs) which are able to identify such interaction.

In such screens, existing drugs were screened for potential binding to known protein structures of SARS-CoV-2, thereby identifying, besides known virustatic agents, the anti-ulcer drug, Famotidine, as a possible 3CLpro-protease blocker of SARS-CoV-2 (Wu C, Liu Y, Yang Y, Zhang P, Zhong W, Wang Y, Wang Q, Xu Y, Li M, Li X, Zheng M, Chen L, and Li H (2020) Analysis of therapeutic targets for SARS-CoV-2 and discovery of potential drugs by computational methods. *Acta Pharm Sin B, doi:* 10.1016/j.apsb.2020.02.008.) and several antibiotics as possible blockers of the RNA-dependent RNA polymerase (Pokhrel R, Chapagain P, and Siltberg-Liberles J (2020) Potential RNA-dependent RNA polymerase inhibitors as prospective therapeutics against SARS-CoV-2. *J Med Microbiol*, doi:

10.1099/jmm.0.001203.) as also other small molecules as blockers of the RNA-dependent RNA polymerase (Aftab S O, Ghouri M Z, Masood M U, Haider Z, Khan Z, Ahmad A, and Munawar N (2020) Analysis of SARS-CoV-2 RNA-dependent RNA polymerase as a potential therapeutic drug target using a computational approach. *Journal of Translational Medicine* 18:275.).

Along the same lines, the skilled person would be able to take any available collection or library of small molecules, either as bulk library or sub-grouped by specific affinities, features or requirements, and run high-throughput analyses, e.g. based on surface plasmon resonance, against any of the newly identified peptide epitopes of SEQ ID NO: 9 or 10 as targets. In so doing, novel small molecules exhibiting specific binding to the new epitopes can be identified without an undue burden and using standard procedures commonly known in the art.

Exemplary collections of small molecules which may preferably be used are the ChemBridge DIVERSet-CL and -EXP collections from ChemBridge Corporation, San Diego, CA, USA, the Maybridge Screening Collection (in the form of Maybridge HitDiscover, Maybridge HitFinder or Maybridge HitCreator) from Thermo Fisher Scientific, Geel, Belgium, the Antiviral Screening Library (Supplier/Item Nr. 30390-50) or the SARS-CoV-2 Screening Library (Supplier/Item Nr. 9003509) from Cayman Chemical, Ann Arbor, MI, USA, or any Diversity Set of University of Cincinnati Compound Collections, or any other available collection or library of suitable small molecules as deemed useful by a skilled person.

In another preferred embodiment of the sixth aspect of the present invention, the affinity molecule is a peptide-based compound, more preferably an antibody or a binding fragment thereof.

In order to raise novel antibodies or binding fragments of such antibodies, it is easy, straightforward and common practice to generate effective monoclonal antibodies by using the established and reliable hybridoma technology against the newly identified peptide epitopes. while e.g. immunizing an animal with the corresponding peptide sequence. While it is probable that for the treatment of a viral disease not the full antibody (about 150 kDa) will be administered, fragments such as e.g. Fab-fragments or even smaller parts derived from an antibody may be used for therapy, in order to be able to reach the target in vivo.

Such binding fragments may consist of or comprise Fab, Fab', Fab'-SH, F(ab)$_2$, Fv, a diabody, single chain antibody fragment or other fragments having the specific affinity to the epitope. In this regard, within the present invention, an affinity molecule specifically binding to or directed against the newly found epitopes of SEQ ID NO: 9 or 10 means an affinity molecule binding to said target epitopes with an at least 10-fold, preferably at least 50-fold, more preferably at least 100-fold increased affinity compared to unrelated epitopes, proteins or protein regions.

According to a preferred embodiment of the present invention, specific binding of an affinity molecule to the isolated target epitopes is considered to be given at a $K_D$ of less than 500 µM, preferably less than 200 µM, more preferably less than 100 µM, when measured by isothermal titration calorimetry as further described below. According to another preferred embodiment of the present invention, specific binding of an affinity molecule to the full-length RNA-dependent RNA polymerase is considered to be given at a $K_D$ of less than 1 mM, preferably less than 100 µM, more preferably less than 10 µM, when measured by isothermal titration calorimetry as further described below. Alternatively preferably, affinity measurements for determination of $K_D$ values may be carried out using the Biacore™ assay from GE Healthcare Life Sciences according to the Biacore Assay Handbook 29-0194-00 Edition AA, or any other affinity measurement as known in the art.

In one other preferred embodiment of the sixth aspect of the present invention, the affinity molecule is an aptamer or oligonucleotide. As is the case for antibodies, there are procedures to generate specifically binding oligonucleotide molecules to targets which are accessibly and can easily be employed in such assays.

SELEX as one of these technologies for finding novel oligonucleotide binders to a known epitope was used and described as early as 1990. Today, many different SELEX-based aptamer selection procedures are developed and are in use (Ali M H, Elsherbiny M E, and Emara M (2019) Updates on Aptamer Research. *International Journal of Molecular Sciences* 20.) which altogether enabled the selection of aptamers to almost all thinkable targets (Stoltenburg R, Nikolaus N, and Strehlitz B (2012) Capture-SELEX: Selection of DNA Aptamers for Aminoglycoside Antibiotics. *Journal of Analytical Methods in Chemistry* 2012:415697.).

Since the first publication of aptamers in 1990, aptamers have been described for a wide variety of different classes of targets from small molecules, like nucleotides, cofactors or amino acids, over peptides, polysaccharides and proteins to complex structures like whole cells, viruses and single cell organisms (cf. for example Zhang Y, Lai B S, and Juhas M (2019) Recent Advances in Aptamer Discovery and Applications. *Molecules* 24.).

In this regard, the provision of novel epitopes within a key enzyme of Coronaviridae viruses enables the skilled person to generate additional affinity molecules such as small molecules, antibody-derived compounds as well as aptamers by using standard procedures as commonly known in the art. Such additional affinity molecules are considered plausible active agents for fighting infection with SARS-CoV-2 due to their specific binding to a yet unknown site within a key enzyme of the virus, thus interfering with the viral replication cycle.

All embodiments of the present invention as described herein are deemed to be combinable in any combination, unless the skilled person considers such a combination to not make any technical sense.

EXAMPLES

1. NMR Analysis of the Interaction Between BC007 and a Sequence Motif of the Receptor-Binding Domain (RBD) of SARS-CoV-2

All NMR spectra were acquired at 600 MHz on a Bruker AV600 spectrometer (Bruker Biospin, Rheinstetten, Germany) in 90/10 $H_2O/D_2O$ at 298K. The solvent signal was suppressed using Watergate w5 pulse sequence included in the Bruker pulse program zggpw5. Acquisition parameters included: time domain=65K, number of scans=512, sweep width=24 ppm and 90° high power pulse=13.8 μs.

The concentration of BC007 and the peptide of SEQ ID NO: 5 was 1 mM. Substances were dissolved in 0.5 ml pure $H_2O/D_2O$ mixture without any additives.

The upper NMR spectrum in FIG. 1 of BC007 in combination with the peptide of SEQ ID NO: 5 from the Receptor-binding domain of the Spike protein from SARS-CoV-2 (upper spectrum) shows formation of the quadruplex structure of BC007 induced by interaction with the peptide and clearly recognizable by eight imino signals at 12.5 ppm; the peptide signals in the spectrum are strongly shifted and broadened in comparison to the potassium-induced fold, an effect that is caused by the interaction of the two molecules (peptide with BC007).

In the lower NMR spectrum in FIG. 1, the imino signals in the range of 12 ppm are again a clear indication of the structure formation induced by the presence of potassium ions, the chemical shifts of the imino protons however clearly differ from those of the upper spectrum. No imino signals in the range of 12 ppm are observed for the peptide alone (middle spectrum).

The aptamer of SEQ ID NO: 1 has previously been reported to be stabilized in its characteristic fold in the presence of potassium ions (Schultze, P. et al., 1994. Three-dimensional solution structure of the thrombin-binding DNA aptamer d(GGTTGGTGTGGTTGG). J. Mol. Biol. 235, 1532-1547. https://doi.org/10.1006/jmbi.1994.1105) and to be present in a predominantly random coil structure in water (cf. Weisshoff, H. et al., 2018. Characterization of Aptamer BC 007 Substance and Product Using Circular Dichroism and Nuclear Magnetic Resonance Spectroscopy. J Pharm Sci. https://doi.org/10.1016/j.xphs.2018.04.003).

Figure 2:
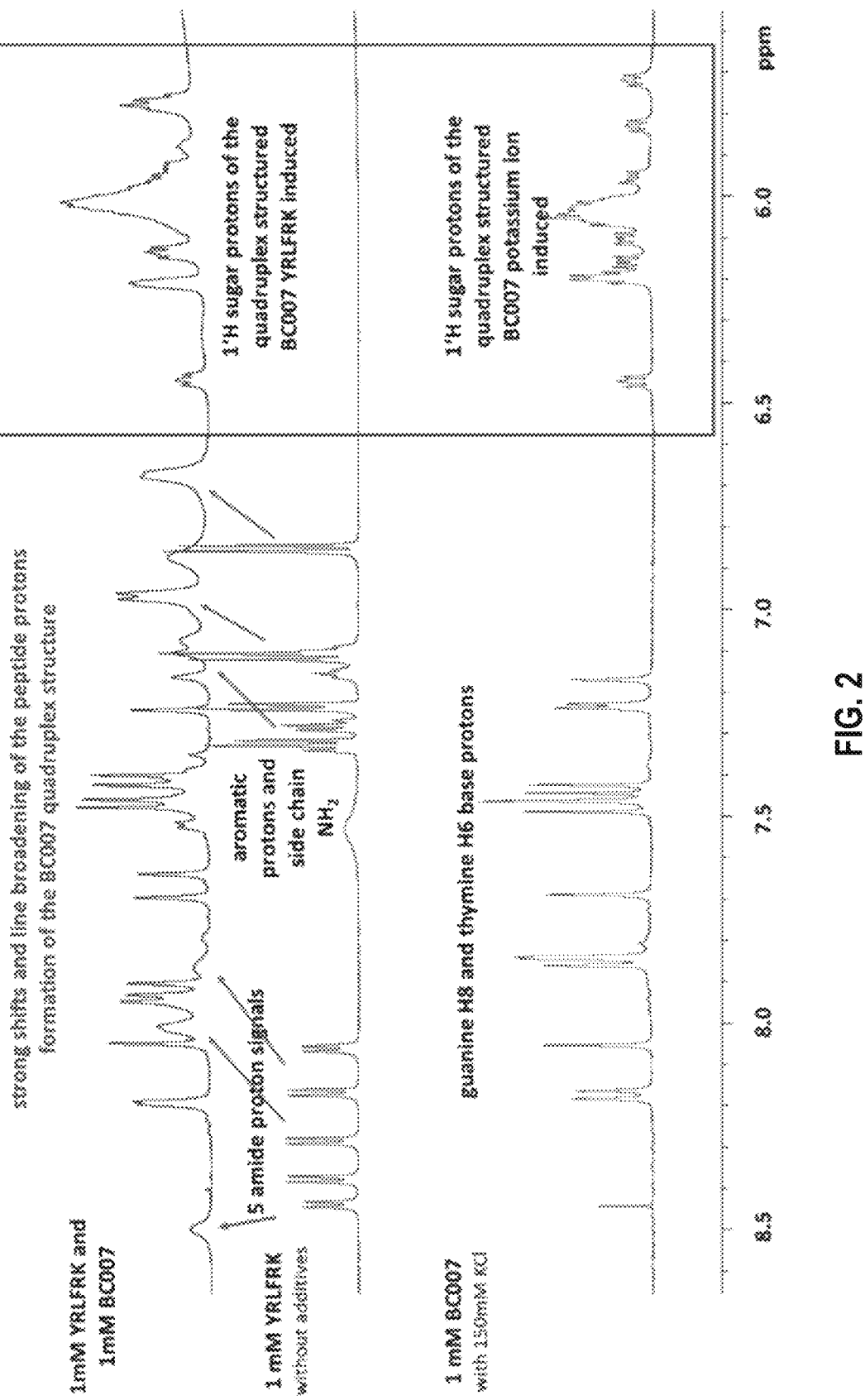
FIG. 2 shows the same spectra of FIG. 1, wherein the view is zoomed into the range between 8.5-6.0 ppm; middle and bottom: pure substances show rather sharp signals, which are broadened and shifted in their position in the upper spectrum due to the interaction of the two substances with each other.

In the enlarged view of FIG. 2, it can be seen how the peaks present for each molecule alone are based on very sharp signals. These signals are then broadened and shifted in their position in the upper spectrum due to the strong interaction between the aptamer of SEQ ID NO: 1 as the agent thought to be active against Coronavirus and SEQ ID NO: 5 as a representative sequence from the Receptor-binding domain of the Spike protein of SARS-CoV-2.

Based on these results, it is expected that said interaction also occurs under in vivo conditions, with the complete virus material and other strains of the same family of Coronaviridae which also use Spike proteins and their Receptor-binding domains for cell entry and infection.

2. Inhibition of SARS-CoV-2 Replication by BC 007 in Human and Primate Cell Lines Investigation of the antiviral dose-response effect of BC 007 was carried out in VeroFM and Calu-3 cells. The aptamer BC 007 of SEQ ID No. 1 was added to the virus at different concentrations and kept for 15 min at 4° C., before the mixture was added onto the cells (to a MOI 0.0005) and warmed up to 37° C. for 30 min in order to start virus attachment and entry.

After this 30 min incubation, supernatants were removed, cells were washed once with PBS and medium containing the same final concentration of BC 007 was added after washing. After an incubation of 24 hrs at 37° C. (replication), a sample aliquot for each concentration was taken for the plaque assay which was carried out as described previously (Herzog et al., *Virology Journal* 2008, 5:138).

Figure 3:
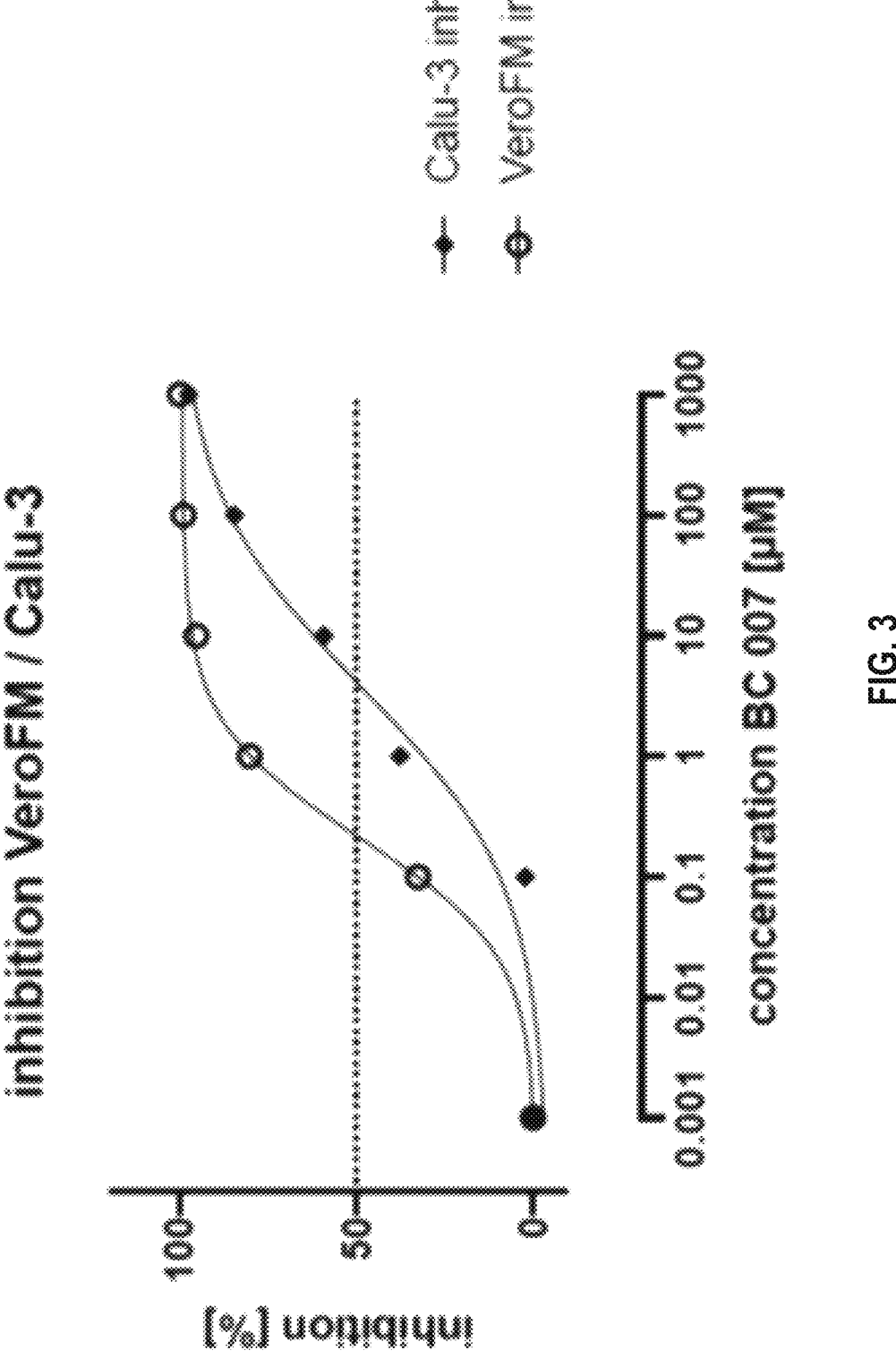
FIG. 3 shows inhibition of SARS-CoV-2 replication by BC 007 in cell culture based on antiviral dose-response effects of BC 007 in VeroFM and Calu-3 cells.

BC007 demonstrated highly efficient inhibition of virus replication at low doses in Vero as well as Calu-3 cell lines (see FIG. 3). Half-maximal effective concentrations ($EC_{50}$, alternatively termed half-maximal inhibitory concentration $IC_{50}$) determined for inhibition of viral infection of were at 3.74 μM for Calu-3 cells and 0.21 μM for Vero cells.

For a comparison to other antiviral agents implicated for potential treatment of SARS-CoV-2, reference is made to the publication of Wang et al., *Cell Research* 2020, 30:269-271. Therein, ribavirin, penciclovir, favipiravir, nitazoxanide, chloroquine and remdesivir were tested in a similar experimental setup using Vero E6 cells and a starting MOI of 0.05.

In this report of Wang et al., the $EC_{50}$ concentrations were determined as 109.50 μM for ribavirin, 95.96 μM for penciclovir, 61.88 μM for favipiravir, 2.12 μM for nitazoxanide, 1.13 μM for chloroquine and 0.77 μM for remdesivir (see full paragraph bridging left-hand column and right-hand column on page 269 and FIG. 1a on page 270 of Wang et al., 2020).

Based on the results obtained with remdesivir, it was concluded that remdesivir potently blocked virus infection at low-micromolar concentration. Further, remdesivir lacked substantial cell-toxicity at the concentrations used for testing its SARS-CoV-2 inhibiting effect.

In view of the results reported in Wang et al., 2020, it becomes clear that the results obtained in Vero cells with the aptamer of the present invention also demonstrate potent blockage of virus infection up to or even beyond the efficiency observed with other antiviral agents currently discussed as potential treatment options for Coronaviridae infections.

Importantly, and in analogy to the molecules identified to perform very well in Wang et al., 2020, the aptamer of the present invention not only showed efficient inhibition of infectious activity of SARS-CoV-2 on Vero and moreover also on human cells (Calu-3), but also lacked any toxicity as already shown in a successfully completed phase I of clinical testing (Becker et al., *Clin Drug Investig* 2020 May; 40(5):433-447) at the doses intended and required for the observed inhibition of SARS-CoV-2 in human cells.

The striking advantage of the aptamer of the present invention over remdesivir as a presently discussed treatment option is the simplicity and ease of preparation of said aptamer. Remdesivir as an example for antiviral agents suggested for treatment of Coronaviridae infections had been reported as requiring about 70 raw materials, reagents and catalysts, some of which are highly dangerous to human (cf. Langreth, Robert (14 May 2020). "All Eyes on Gilead". Bloomberg Businessweek. Bloomberg, L.P.).

Furthermore, the synthesis apparently involves approximately 25 time-consuming chemical steps leading to a required time for the original end-to-end manufacturing process of 9 to 12 months to go from raw materials at contract manufacturers to the finished product.

In contrast, the aptamer of the present invention which may be used and administered as an unmodified DNA molecule can be produced on a large scale up to kilogram amounts satisfying global needs in a matter of weeks for a fraction of the costs involved for comparative antiviral agents such as remdesivir.

Figure 4:
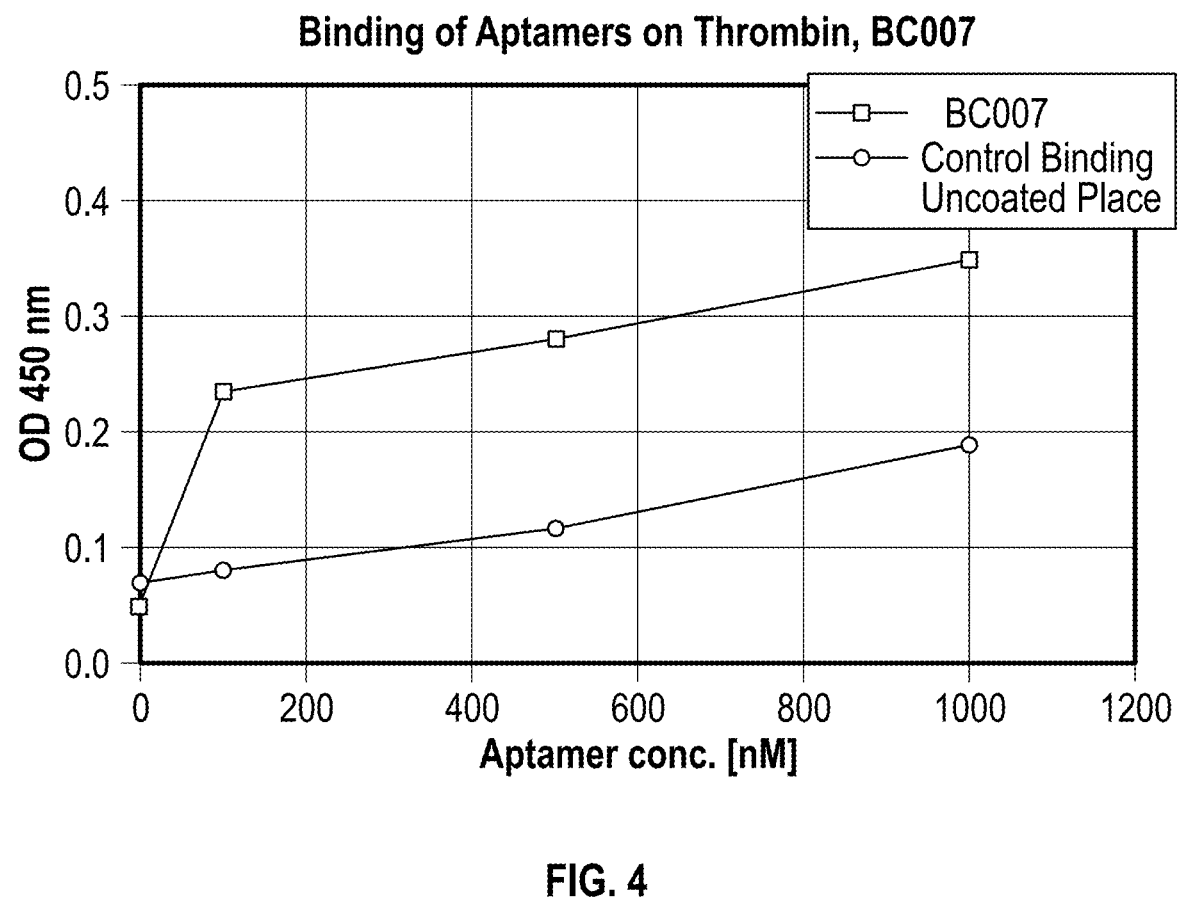

3. Interaction Between BC007 and Human Thrombin and Consequent Inhibition of Coagulation Human thrombin (250 nM) is immobilized with 0.1 M carbonate buffer overnight at 4° C. on Nunc Maxisorp ELISA-plates and then blocking is carried out with 1% BSA in phosphate buffered saline solution (PBS), pH 7.4, for 1 hr at room temperature. Then, 5'-biotinylated aptamer BC007 is added in various concentrations (100 nM, 500 nM and 1000 nM) and incubated for 2 hours at room temperature. Aptamer bound to thrombin is detected via POD-coupled Neutravidine, wherein the amount of POD is determined via hydrogen peroxide/tetramethylbenzidine (TMB) reaction and readout is performed with a plate reader at a wavelength of 450 nm=measuring wave length (650 nm reference wave length). Washing is carried out between each using routine ELISA-washing buffer; thrombin-free plastic plates serve as controls. Results of the thrombin binding assay are shown in FIG. 4.

For the determination of coagulation inhibition, partial thromboplastin time (PTT) was measured as follows. 50 μl of a 1 mM aptamer solution (BC007 of SEQ ID NO:1 or aptamer AS1411 of SEQ ID NO: 7 as reference aptamer) was diluted in 1 mL HemosIL human calibration plasma ((Instrumentation Laboratory, Werfen). This solution was then further serially diluted 1:2 to concentrations of 0.083, 0.028, 0.009, 0.003, 0.001 mg/ml in HemosIL calibration plasma.

These samples were incubated with phospholipids and buffer according to the manufacturer's protocol. After the addition of calcium, the time to coagulation was measured with an ACL TOP Coagulation system (Werfen). Results are shown in FIG. 5A.

Quick values of aptamer BC007 and reference aptamer AS1411 of SEQ ID NO: 7 were determined as commonly known in the art. Results are shown in FIG. 5B (Quick value).

4. Analysis of the Interaction Between BC007 and Two Sequence Motifs of the RNA-Dependent RNA Polymerase of SARS-CoV-2

Two sequence sections taken from RNA-dependent RNA polymerase of Severe acute respiratory syndrome coronavirus 2 (NCBI Reference Sequence: YP_009725307.1): HRFYRLAN ($His^{650}$-$Arg^{651}$-$Phe^{652}$-$Tyr^{653}$-$Arg^{654}$-$Leu^{655}$-$Ala^{656}$-$Asn^{657}$) and LYRNRDV ($Leu^{731}$-$Tyr^{732}$-$Arg^{733}$-$Asn^{734}$-$Arg^{735}$-$Asp^{736}$-$Val^{737}$) were analysed for binding and interaction with BC007 via NMR-spectroscopy. Both sequence sections (peptides) were able to force BC 007 into its well-known quadruple structure (FIG. 6), which is the readout for successful and specific binding.

Figure 6:
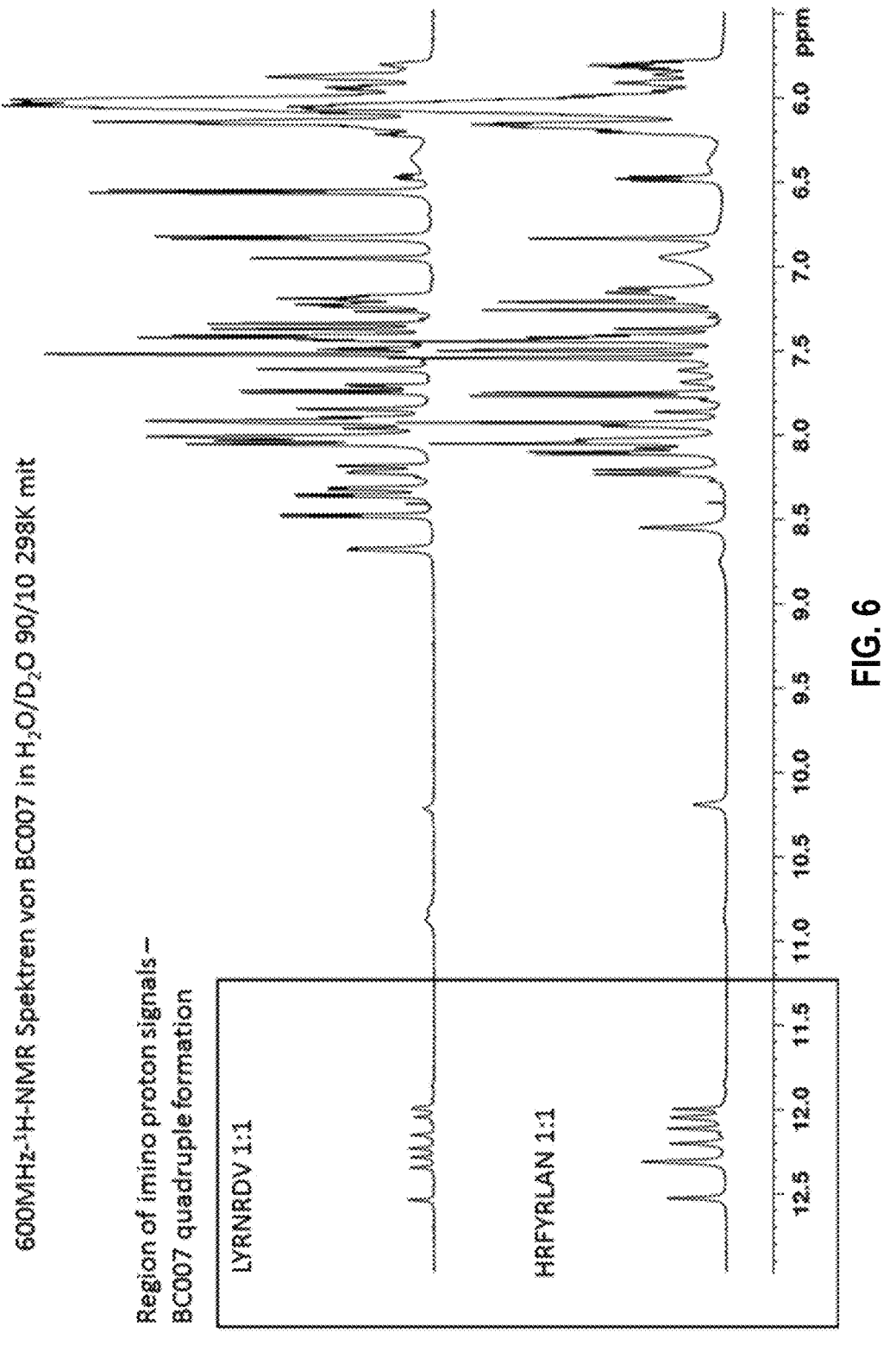
FIG. 6 shows NMR analysis of quadruplex formation of BC007 in the presence of peptide LYRNRDV (top; SEQ ID NO: 9) and peptide HRFYRLAN (bottom; SEQ ID NO: 10) of the RNA-dependent RNA polymerase of SARS-CoV-2 (full-length sequence as SEQ ID NO: 8), wherein both peptides were able to induce the quadruplex fold which is indicative for successful and specific binding.

The upper NMR spectrum of BC 007 in combination with LYRNRDV in the upper part of FIG. 6 shows formation of the quadruplex structure of BC 007 induced by molecular interaction with the peptide which is clearly recognisable by the imino signals between 11.5 and 12.5 ppm. The lower spectrum shows the binding between BC 007 and HRFYRLAN.

Substances were dissolved in 0.5 ml pure $H_2O/D_2O$ mixture without any additives. The NMR data investigating the interaction of BC 007 with these sequence-sections of SARS-CoV-2 proteins were acquired at 600 MHz on a Bruker AV600 spectrometer (Bruker Biospin, Rheinstetten, Germany) in 90/10 $H_2O/D_2O$ at 298K. The solvent signal was suppressed using the Watergate w5 pulse sequence included in the Bruker pulse program zggpw5. Acquisition parameters included: time domain=65K, number of scans=512, sweep width=24 ppm and 90° high power pulse=13.8 μs.

Figure 7:
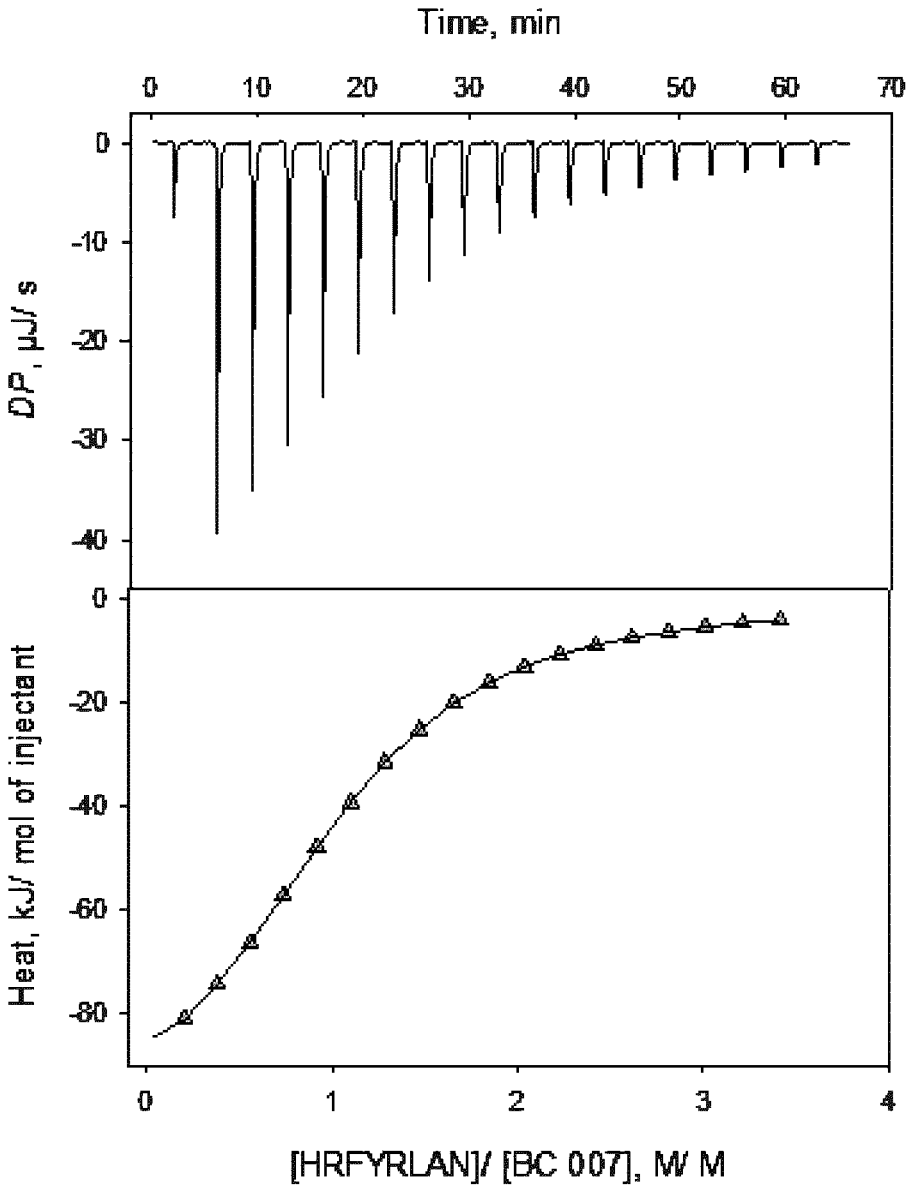
FIG. 7 shows an ITC (isothermal titration calorimetry) analysis of BC007 titrated with peptide HRFYRLAN (SEQ ID NO: 10) of the RNA-dependent RNA polymerase of SARS-CoV-2; top—thermogram; bottom—binding isotherm.

Further analysis of the binding between HRFYRLAN and BC007 was performed by isothermal titration calorimetry (ITC). The results of this ITC analysis are shown in FIG. 7, wherein the thermogram is in the upper part and the binding isotherm in the lower part.

The ITC experiments were performed on MicroCal PEAQ-ITC microcalorimeter (Malvern Panalytical GmbH, Germany). Both interaction partners were solved in 50 mM sodium phosphate, 150 mM NaCl buffer, pH 7.06. Experiments were carried out at 25° C. In routine experiments, peptide (3.6 or 4 mM) was titrated in 2 μl-steps into aptamer solution (200 μM) in the calorimeter cell. Time intervals between the injections were adjusted to 200 sec, which was sufficient for the heat signal to return to baseline. Reaction mixtures were continuously stirred at 750 rpm.

Dilution heats associated with the addition of the peptides into buffer (determined in separate control experiments) had small constant values that were negligible to measured binding heats. The instrument software (MicroCal PEAQ-ITC Analysis) was used for baseline adjustment, peak integration and normalization of the reaction heats with respect to the molar amount of injected ligand as well as for data fitting and binding parameter evaluation.

This ITC analysis revealed a 1:1 stoichiometric binding between the two binding partners BC007 and HRFYRLAN which strongly supports a true and specific binding.

Figure 8:
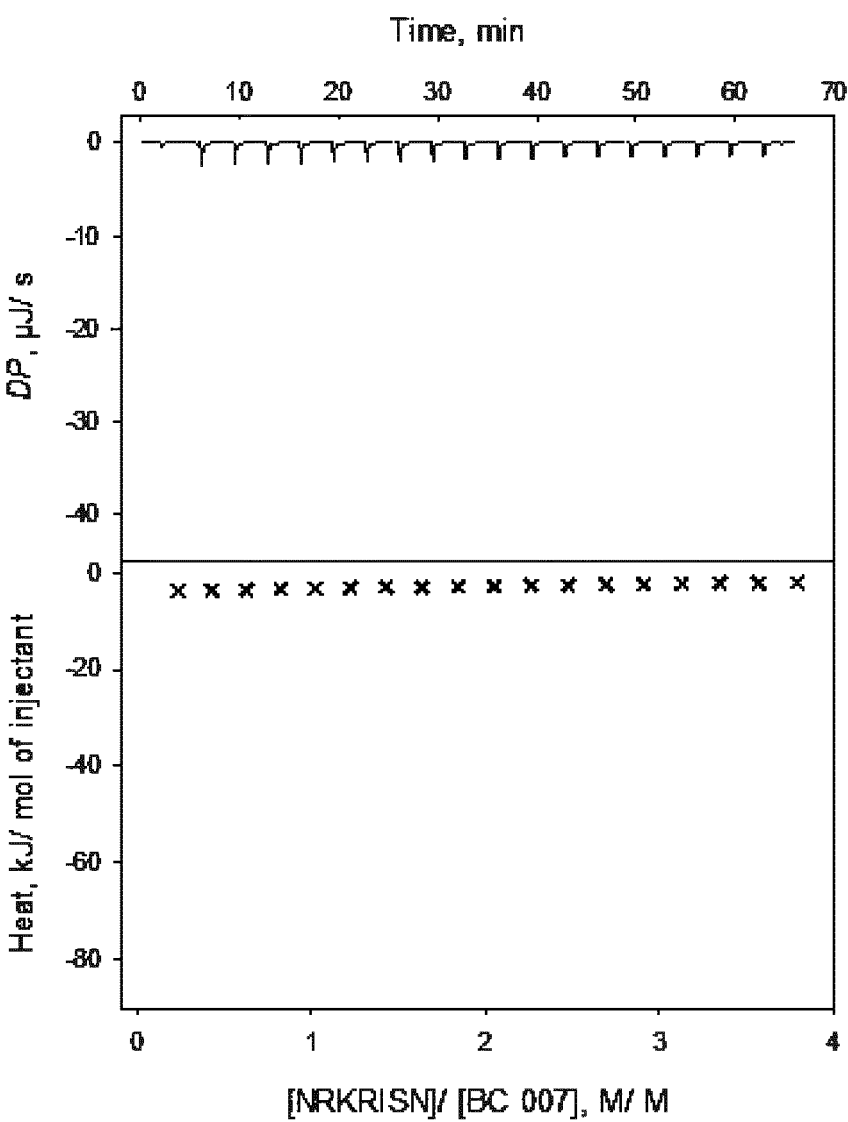
FIG. 8 shows ITC analysis of BC007 titrated with a comparative, highly charged peptide control sequence, NRKRISN (SEQ ID NO: 11), which is also present in the Spike RBD of SARS-CoV-2; top—thermogram; bottom—binding isotherm.

A control experiment for the ITC analysis was run using a highly charged peptide from the Spike RBD of SARS-CoV-2 having the sequence NRKRISN (SEQ ID NO:11; theoretical pI value of 12.01). The results are shown in FIG. 8. With this control, a sole non-specific electrostatic interaction between the binding peptides of the RNA-dependent RNA polymerase HRFYRLAN (theoretical pI value of 10.84) and LYRNRDV (theoretical pI value of 8.75) and BC 007 could clearly have been excluded.

The experiments were again performed on MicroCal PEAQ-ITC microcalorimeter (Malvern Panalytical GmbH, Germany). Both interaction partners were solved in 50 mM sodium phosphate, 150 mM NaCl buffer, pH 7.16. Experiments were carried out at 25° C. In routine experiments, peptide (3.6 or 4 mM) was titrated in 2 µl-steps into aptamer solution (200 µM) in the calorimeter cell. Time intervals between the injections were adjusted to 200 sec, which was sufficient for the heat signal to return to baseline. Reaction mixtures were continuously stirred at 750 rpm. Dilution heats associated with the peptides-addition into buffer (determined in separate control experiments) had small constant values that were negligible to measured binding heats. The instrument software (MicroCal PEAQ-ITC Analysis) was used for baseline adjustment, peak integration and normalization of the reaction heats with respect to the molar amount of injected ligand as well as for data fitting and binding parameter evaluation.

Figure 9:
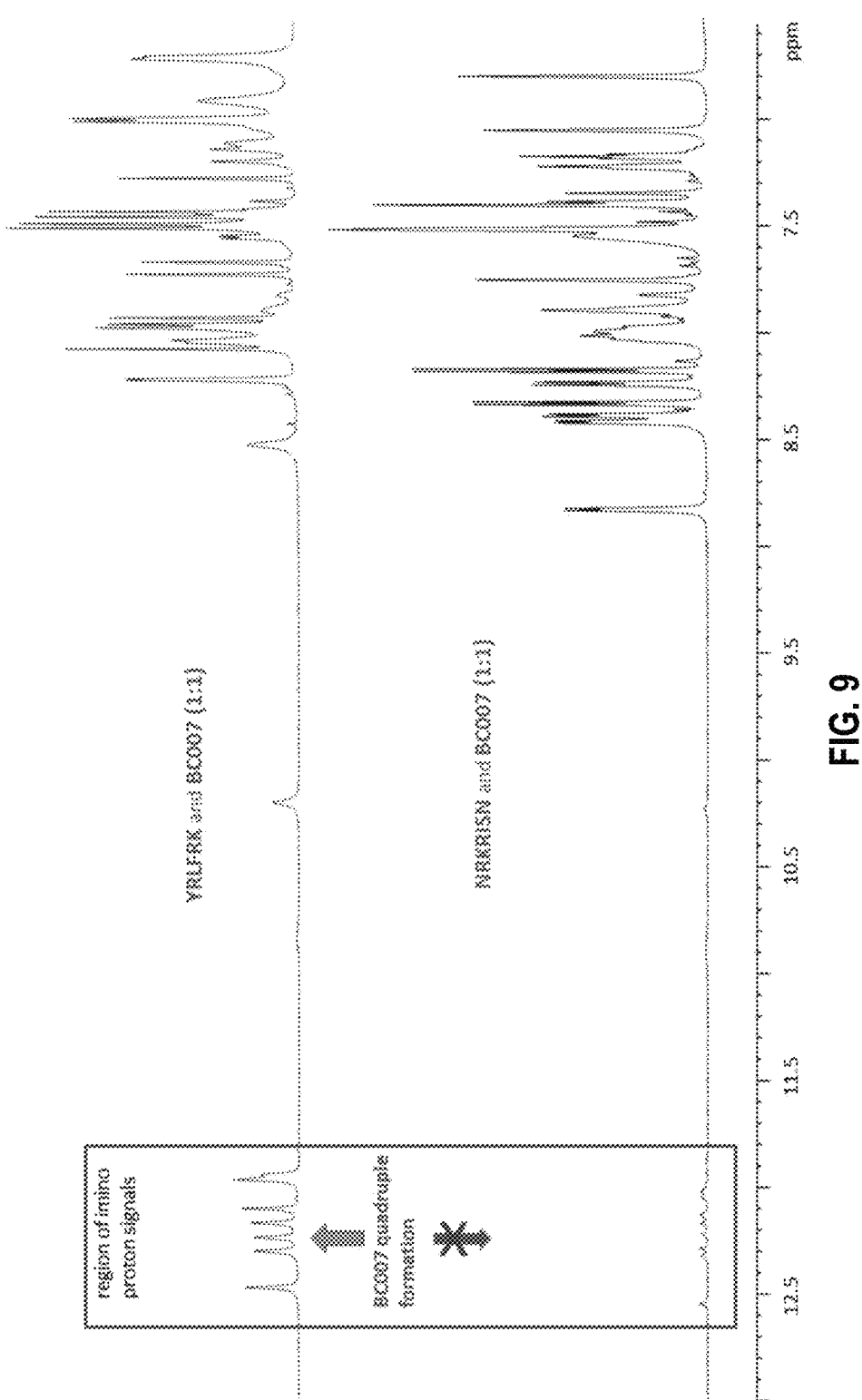
FIG. 9 shows a comparison of NMR analyses of BC007 in the presence of control peptide NRKRISN (SEQ ID NO: 11), and peptide No. 4 (SEQ ID NO: 5; YRLFRK) from the spike protein of SARS-CoV-2.

Finally, NMR spectroscopy was also carried out to analyse potential binding of BC007 to the control peptide, NRKRISN. The results thereof are shown in FIG. 9. The NMR spectrum of BC 007 in combination with NRKRISN demonstrates the nearly complete absence of formation of the quadruplex structure of BC 007, recognizable in the missing imino signals between 11.5 and 12.5 ppm. For comparison: upper spectrum: BC 007 binding of the peptide sequence YRLFRK (sequence from the spike protein of SARS-CoV-2, theoretical pI value of 11.0).

Substances were dissolved in 0.5 ml pure H2O/D2O mixture without any additives. The NMR data investigating the interaction of BC 007 with this sequence-section of a SARS-CoV-2 protein was acquired at 600 MHz on a Bruker AV600 spectrometer (Bruker Biospin, Rheinstetten, Germany) in 90/10 H2O/D2O at 298K. The solvent signal was suppressed using the Watergate w5 pulse sequence included in the Bruker pulse program zggpw5. Acquisition parameters included: time domain=65K, number of scans=512, sweep width=24 ppm and 90° high power pulse=13.8 µs.

5. Identification and Characterization of GPCR Autoantibodies in Sera of Patients Having Recovered from Active SARS-CoV-2 Infections Sera were obtained from 25 patients after recovery from acute disease as confirmed by PCR. 23 patients were suffering from post-COVID-19 symptoms, while 2 patients were symptom-free.

As a safety-precaution, the COVID-19 patient sera were heat inactivated for 30 min at 56° C. before use. Afterwards, 0.4 mL of the samples were dialysed against 1 L of dialysing buffer (0.15 M NaCl, 10 mM phosphate buffer, pH 7.4; Membra-Cel MD 44, 14 kDa, Serva) for 24 hours to remove low-molecular weight bioactive compounds and peptides. Finally, 40 µL of the dialysed samples were added to the bioassay (final dilution of 1:50).

For the identification and characterisation of GPCR-fAABs, a bioassay was used, as described in great detail by Davideit et al. (Davideit H et al (2019) Determination of Agonistically Acting Autoantibodies to the Adrenergic Beta-1 Receptor by Cellular Bioassay. Methods Mol Biol 1901:95-102. https://doi.org/10.1007/978-1-4939-8949-2_8) and Wenzel et al. (Wenzel K, Schulze-Rothe S, Haberland A, et al (2017) Performance and in-house validation of a bioassay for the determination of beta1-autoantibodies found in patients with cardiomyopathy. Heliyon 3:e00362. https://doi.org/10.1016/j.heliyon.2017.e00362) for GPCR-fAABs against the beta1-adrenoceptor, and analogously for other GPCR-fAABs (see also Wallukat et al. (2018) *PLoS ONE* 13:e0192778) for the parallel determination of several GPCR-fAABs After contact with the respective autoantibodies, a change in basal beating rate of spontaneously beating cardiomyocytes expressing GPCR was used as the measuring signal. The receptor specificity was checked by either subsequent addition of specific receptor blockers, resulting in an annulation of this effect, or by addition of corresponding receptor-epitope-competing extracellular loop peptides. In detail: for the specification of the β2-fAABs, the receptor antagonist ICI118.551 (0.1 µM) was used and also neutralizing peptides corresponding to the first or second extracellular loop of the human β2-adrenoceptor.

The effect of the negative chronotropic muscarinic M2 receptor-autoantibody (M2-fAAB) was blocked by atropine (1 µM). Losartan (1 µM) blocked the effect of the positive chronotropic AT1-fAAB and A779 (1 µM) blocked the effect of the negative chronotropic MAS-fAAB. For the identification of the MAS-fAAB, additional competing peptides corresponding to the first and second extracellular loop of the human MAS receptor were exploited.

ETA-fAABs were identified by blocking their negative chronotropic effects through the addition of the specific endothelin receptor antagonist BQ123 (0.1 µM) and also competing peptides corresponding to the first or second extracellular loop of the receptor, respectively.

The nociceptin receptor antagonist J113397 (0.1 µM) was used to block the effects of the positive chronotropic NOC-fAAB and also competing peptides corresponding to the first or second extracellular loop. Addition of 1 µM urapidil or prazosin abolished the positive chronotropic effect of α1-fAABs. For all peptides 2 µL of a stock solution of 100 µg/mL was added to 40 µL of the corresponding GPCR-fAAB sample and incubated for 30 min before the mixture was transferred to the cells.

Several different GPCR-fAABs were identified in the 25 sera of recovered COVID-19 patients. All 25 investigated patients had between 2 and 7 different GPCR-fAAB (FIG. 10).

Two functionally active autoantibodies that were seen in almost all investigated patients, were directed against the β2-adrenoceptor (β2-fAAB) and the muscarinic M2 receptor (M2-fAAB). These fAABs induced a positive and a negative chronotropic response on their targeted receptors, respectively.

Two other fAABs that were also present in 23 (92%) of the 25 investigated post-COVID-19 patients were directed against the angiotensin II AT1 receptor (fAT1-AAB) and the angiotensin 1-7 MAS receptor (MAS-AAB). These receptors belong to the renin angiotensin system (RAS) and cause a positive and negative chronotropic effect, respectively, when targeted by the respective fAABs.

Post-infection hair loss (alopecia) was experienced by 8 of the recovered patients. In sera of these patients, three additional GPCR-fAABs were discovered: the negative chronotropic ETA-fAAB (4/8, the positive chronotropic NOC-fAAB (5/8), and the positive chronotropic α1-AAB (3/8). Not every alopecia patient showed all three of these GPCR-fAABs. Instead, their occurrence varied, and a pattern is not yet detectable. As shown in FIG. 10, 2 of the 25 investigated post COVID-19 patients developed fAABs without showing any symptoms.

A continuing fatigue-like symptom, persisting long after virus follow-up tests are negative, was a frequently reported impairment in patients of this study (¹⁷⁄₂₅). For patients suffering from a classical coronavirus-independent fatigue syndrome, the occurrence of β2-fAABs, M2-fAABs and, in some cases, also ETA-fAABs has already been reported before.

Here, almost all investigated sera contained β2-fAABs and M2-fAABs. The combination of β2-fAABs and M2-fAABs have also been identified in sera of patients suffering from PoTS and dysautonomia, both of which are conditions now observed in post-COVID-19 patients (3/25 and 2/25, respectively, not overlapping).

Furthermore, this combination of β2-fAABs with M2-fAABs had also been identified before by the inventors, in patients with complex regional pain syndrome (CRPS), in patients suffering from narcolepsy type 1, here additionally with the NOC-fAAB in 9 of 10 cases and in patients with small fibre diseases.

Two of the identified GPCR-fAABs, observed in over 90% of the investigated COVID-19 patient sera (²³⁄₂₅), were directed against receptors of RAS, namely the angiotensin II AT1 receptor and the angiotensin (1-7) MAS receptor. These vasoactive AT1-fAABs had been identified before in patients with malignant hypertension, therapy-resistant hypertension, preeclampsia, and kidney diseases.

---

The invention claimed is:

1. A method of treating a cell infected with a SARs-CoV-2 virus comprising, administering to the cell an effective amount of an aptamer comprising the nucleic acid sequence of SEQ ID NO: 1 (GGT TGG TGT GGT TGG).

2. The method of claim 1, wherein the aptamer is administered in vitro/ex vivo.

3. The method of claim 1, wherein the aptamer prolongs coagulation time measured as partial thromboplastin time (PTT) of human calibration plasma to 60 seconds or more at an aptamer concentration of 0.03 mg/ml.

4. The method of claim 1, wherein the aptamer lowers the prothrombin time (Quick value) of human calibration plasma to 40% or less at an aptamer concentration of 0.03 mg/ml.

5. The method of claim 1, wherein the aptamer interferes with the infection of somatic cells by selectively interacting with the Spike (S) glycoprotein of the virus.

6. The method of claim 1, wherein the aptamer interferes with the infection of somatic cells by interfering with the interaction of the Spike glycoprotein of the virus and the angiotensin-converting enzyme 2 (ACE2) of a subject host cell.

7. The method of claim 1, wherein the aptamer interferes with a Receptor-binding domain of the Spike glycoprotein having a sequence of SEQ ID NO: 2 (SARS-CoV-2 Spike RBD) or SEQ ID NO: 3 (SARS-CoV Spike RBD), SEQ ID NO: 4 (MERS-CoV Spike RBD), SEQ ID NO: 2 or SEQ ID NO: 3.

\* \* \* \* \*